(12) United States Patent
Mihashi et al.

(10) Patent No.: US 7,568,800 B2
(45) Date of Patent: Aug. 4, 2009

(54) APPARATUS AND METHOD FOR SPECTRALLY MEASURING FUNDUS

(75) Inventors: Toshifumi Mihashi, Tokyo (JP); Yoko Hirohara, Tokyo (JP)

(73) Assignee: Topcon Corporation, Tokyo (JP)

( * ) Notice: Subject to any disclaimer, the term of this patent is extended or adjusted under 35 U.S.C. 154(b) by 0 days.

(21) Appl. No.: 11/812,079

(22) Filed: Jun. 14, 2007

(65) Prior Publication Data
US 2008/0007691 A1 Jan. 10, 2008

(30) Foreign Application Priority Data
Jun. 15, 2006 (JP) ............... 2006-166691

(51) Int. Cl.
*A61B 3/14* (2006.01)
(52) U.S. Cl. .................. 351/206; 351/210
(58) Field of Classification Search ......... 351/205–206, 351/210
See application file for complete search history.

(56) References Cited

U.S. PATENT DOCUMENTS

| 2006/0276698 A1 | 12/2006 | Halldorsson et al. | |
| 2007/0002276 A1* | 1/2007 | Hirohara et al. | 351/206 |

FOREIGN PATENT DOCUMENTS

| JP | 8-071045 A | 3/1996 |
| JP | 2001-145604 A | 5/2001 |
| JP | 2006-158547 A | 6/2006 |

OTHER PUBLICATIONS

U.S. Appl. No. 11/812,081, filed Jun. 14, 2007, Mihashi et al.
T. Mihashi et al., U.S. PTO Office Action, U.S. Appl. No. 11/812,081, May 12, 2008, 20 pgs.
T. Mihashi et al., U.S. PTO Office Action, U.S. Appl. No. 11/812,081, Nov. 25, 2008, 17 pgs.

* cited by examiner

*Primary Examiner*—Scott J Sugarman
*Assistant Examiner*—Dawayne A Pinkney
(74) *Attorney, Agent, or Firm*—Foley & Lardner LLP

(57) ABSTRACT

To provide a spectroscopic fundus measuring apparatus capable of identifying each part in spectral fundus images easily and accurately based on its spectral characteristic and a measuring method therefor. A spectral fundus image measuring apparatus 1 of the present invention includes: an illumination optical system 10; a light receiving optical system 20 for photographing a series of spectral fundus images of different wavelengths; an image processing section 7 for processing the spectral fundus images; a storage section 7A; and a display section 7B. The image processing section 7 has a position correcting section 72 for correcting the series of spectral fundus images to match the positions of the same parts therein, and an image analyzing section 73 for calculating the spectral characteristic of each part in the spectral fundus images based on the series of spectral fundus images corrected in the position correcting section 72. The storage section 7A stores the spectral characteristics of the parts together with standard spectral characteristics of specific parts. The image processing section 7 has a first grouping section 74A for comparing the spectral characteristic of each part with the standard spectral characteristics of the specific parts to divide the parts into groups corresponding to the specific parts.

12 Claims, 15 Drawing Sheets

LIQUID CRYSTAL WAVELENGTH TUNABLE FILTER

IMAGE PROCESSING TO DETECT BLOOD VESSELS (a) IMAGE FOR DETECTION (b) APPLICATION OF MEAN VALUE FILTER AND THEN LAPLACIAN-GAUSSIAN FILTER (c) APPLICATION OF LABELING, EXPANDING AND THINNING (d) ATTACHMENT OF LABEL (c) PC5 RETINAL BLOOD VESSELS (b) PC3 RETINAL VEINS (a) PC2 CHOROIDAL VESSELS

APPARATUS AND METHOD FOR SPECTRALLY MEASURING FUNDUS

BACKGROUND OF THE INVENTION

1. Technical Field

The present invention relates to a spectroscopic fundus measuring apparatus and a measuring method therefor. In particular, the present invention relates to a spectroscopic fundus measuring apparatus that acquires spectral fundus images to facilitate identification of parts with different spectral characteristics and that can form an image in which every part is clear in consideration of the spectral characteristics thereof, and a measuring method therefor.

2. Related Art

Fundus observation is doubtless important in ophthalmic diagnosis. At present, anomaly findings are obtained by diagnosing the eye fundus by means of colored fundus images, fluorescent contrast images, etc. from a fundus camera. If it is possible to measure quantitatively oxygen saturation degree on the fundus and constituent substances distributed in the retina, there is a possibility of finding out the functions of fine parts of the retina, which is considered to be greatly useful in clinical applications. Further, if spectral distribution of substances in the retina is clarified by spectral analyses, there is a possibility of analyzing the substances in the retina from the spectral images.

However, most of the studies carried out up to now are far from spectral image measurement in full-scale. Full-scale image measurement is considered to meet such conditions as: (a) being capable of obtaining high quality images, and (b) being capable of measuring spectral images with a higher degree of wavelength analysis over a wide wavelength band. Such an image measurement method is occasionally called hyper-spectral imaging. Advent of the liquid crystal wavelength tunable filter has made it possible to obtain spectral images relatively easily. Using a number of spectral images of different wavelengths makes it possible to examine spectral characteristics of substances in detail and to extract constituents having various known spectral distributions.

As a technique for identifying each part in a fundus image, a method for distinguishing retinal arteries and retinal veins based on red and green components in a fundus image has been disclosed. Also, a technique where the light beam reflected from a fundus is divided by wavelength into light beams within at least two wavelength regions in a wavelength range of 600 nm or more by a wavelength dividing means, fundus images of different wavelengths are photographed separately by a fundus photographing means, and a plurality of fundus images of different colors are superimposed to display one color image by a displaying means has been disclosed (see Patent Documents 1 and 2).

[Patent Document 1] JP-A-2001-145604 (paragraphs 0024 to 0091, FIG. 1 to FIG. 20)
[Patent Document 2] JP-A-Hei 8-71045 (paragraphs 0011 to 0032, FIG. 1 to FIG. 13)

While the hyper-spectral imaging is a technique in the spotlight and is used to obtain spectral images of the fundus, it is hard to perform accurate analyses because the amount of light of spectral images obtained varies greatly by the wavelength. Moreover, the hyper-spectral light separation with a light amount without putting burden on humans has yet to be realized.

A liquid crystal wavelength tunable filter, which was recently developed, is commercially available and can be used in spectroscopic imaging. When it is used, hyperspectral imaging of a retina can be easily achieved. However, as restricted by for example the wavelength tunable time of the liquid crystal wavelength tunable filter and the exposure time of the camera, it takes about 20 seconds to take images at every 10 nm in the wavelength range from 500 nm to 720 nm. Because alignment between the eye and the apparatus varies during that time, there has been another problem that the spectral images taken of the same part are displaced from each other.

The present inventors proposed an apparatus and method for measuring spectral fundus image data that can eliminate position displacement between spectral images of the same part even if change in alignment occurs between the eye and the apparatus with the lapse of time in Japanese Patent Application No. 2004-352093. However, there is still desired a spectroscopic fundus measuring apparatus capable of identifying parts with different spectral characteristics in a spectral fundus image easily and accurately and forming an image in which every part is clear and a method therefor.

An object of the present invention is to provide a spectroscopic fundus measuring apparatus capable of identifying each part in spectral fundus images easily and accurately based on its spectral characteristic and a measuring method therefor.

SUMMARY OF THE INVENTION

To solve the above problem, a spectroscopic fundus measuring apparatus 1 related to aspect (1) of the present invention comprises, as shown in FIG. 1 for example, an illumination optical system 10 having an illumination light source 11 for illuminating a fundus; a light receiving optical system 20 for receiving a wavelength-tunable light beam reflected from the illuminated fundus to photograph a series of spectral fundus images of different wavelengths; an image processing section 7 for processing the spectral fundus images; and a storage section 7A for storing the spectral fundus images, wherein the image processing section 7 has a position correcting section 72 for correcting the series of spectral fundus images photographed by the light receiving optical system 20 to match the positions of the same parts therein, and an image analyzing section 73 for calculating the spectral characteristic of each part in the spectral fundus images based on the series of spectral fundus images corrected in the position correcting section 72, wherein the storage section 7A stores the spectral characteristics of the parts together with standard spectral characteristics of specific parts, and wherein the image processing section 7 has a first grouping section 74A for comparing the spectral characteristic of each part with the standard spectral characteristics of the specific parts to divide the parts into groups corresponding to the specific parts.

Here, a series of spectral fundus images of different wavelengths typically mean a group of spectral fundus images of the same subject eye photographed in succession while increasing or decreasing the wavelength in a predetermined wavelength range. Changes in the photographing order or slight changes in the photographing conditions are acceptable. Processing means image processing including position matching correction among spectral fundus images, transformation such as projective transformation, filtering such as noise removal and edge detection, and expanding and thinning. Grouping typically means dividing parts into groups of different specific parts. Parts with a spectral characteristic which nearly matches but slightly differs from a standard spectral characteristic of a specific part because of deterioration in health or the like may be classified into a different group. Parts which do not match any of the specific parts may be classified into a group of others. The specific parts mean distinctive parts in a fundus image such as retinal arteries, retinal veins, optic nerve head, choroid, and macula area. With the above constitution, there can be provided a spectroscopic fundus measuring apparatus capable of identifying each part in spectral fundus images easily and accurately based on its spectral characteristic.

The invention related to aspect (2) of the present invention is the spectroscopic fundus measuring apparatus related to aspect (1), wherein the first grouping section 74A divides the parts into groups of retinal artery, retinal vein, macula area, optic nerve head and so on as the specific parts.

With this constitution, the parts in the fundus images can be classified into groups of primary parts.

The invention related to aspect (3) is the spectroscopic fundus measuring apparatus related to aspect (1) or (2), wherein the image processing section 7 has a specific part image forming section 76A for collecting respectively the parts divided into groups corresponding to the specific parts to form images of the specific parts.

With this constitution, fundus images regarding the specific parts can be efficiently formed using spectroscopic analysis.

To solve the above problem, a spectroscopic fundus measuring apparatus related to aspect (4) of the present invention comprises, as shown in FIG. 12 for example, an illumination optical system 10 having an illumination light source 11 for illuminating a fundus; a light receiving optical system 20 for receiving a wavelength-tunable light beam reflected from the illuminated fundus to photograph a series of spectral fundus images of different wavelengths; an image processing section 7 for processing the spectral fundus images; and a storage section 7A for storing the spectral fundus images, wherein the image processing section 7 has a position correcting section 72 for correcting the series of spectral fundus images photographed by the light receiving optical system 20 to match the positions of the same parts therein, and a second grouping section 75A for regarding each principal component image formed by a principal component analysis method as a fundus image of a specific part based on the series of spectral fundus images corrected in the position correcting section 72 to divide parts in the spectral fundus images into groups corresponding to the specific parts.

Dividing into groups corresponding to the specific parts typically means dividing parts into groups of different specific parts. Parts with a spectral characteristic which nearly matches but slightly differs from a standard spectral characteristic of a specific part because of deterioration in health or the like may be classified into a different group. Parts which do not match any of the specific parts may be classified into a group of others. With the above constitution, there can be provided a spectroscopic fundus measuring apparatus capable of identifying each part in spectral fundus images easily and accurately based on its spectral characteristic.

The invention related to aspect (5) of the present invention is a spectroscopic fundus measuring apparatus related to aspect (4), wherein the second grouping section 75A regards a choroidal vessel image, a retinal artery image, a retinal vein image and a retinal blood vessel image respectively as corresponding to any one of a second principal component image to a fifth principal component image to divide the parts into groups.

With this constitution, the parts in the fundus images can be classified into groups of primary parts.

The invention related to aspect (6) of the present invention is the spectroscopic fundus measuring apparatus related to aspect (4) or (5), further comprising, as shown in FIG. 1 for example, a display section 7B for displaying the spectral fundus images, wherein the image processing section 7 has an image analyzing section 73 for calculating a spectral characteristic of each part in the spectral fundus images based on the series of spectral fundus images corrected in the position correcting section 72, wherein the storage section 7A stores the spectral characteristics of the parts together with standard spectral characteristics of specific parts, and wherein, when an operator designates a part on the displayed spectral fundus images, the display section 7B displays the spectral characteristic of the designated part stored in the storage section.

With this constitution, the specific parts corresponding to fundus images formed by the principal component analysis can be confirmed with human eyes when the grouping is carried out.

The invention related to aspect (7) is the spectroscopic fundus measuring apparatus related to any one of aspects (1) to (3) and aspect (6), further comprising: a display section 7B for displaying the spectral fundus images, wherein the image analyzing section 73 calculates the contrast between the brightness of each of the parts and the brightness of the background thereof based on the series of spectral fundus images corrected in the position correcting section 72, wherein the storage section 7A stores the contrasts of the parts, and wherein, when an operator designates a part on the displayed spectral fundus images, the display section 7B displays the contrast of the designated part stored in the storage section 7A.

With this constitution, the specific parts can be confirmed based on the contrasts when the grouping is carried out.

The invention related to aspect (8) is the spectroscopic fundus measuring apparatus related to any one of aspects (3) to (7), wherein the image processing section 7 has an image synthesizing section 78 for synthesizing the images of the specific parts to form a synthesized fundus image.

With this constitution, a fundus image in which a plurality of specific parts are clearly visible can be formed.

The invention related to aspect (9) is the spectroscopic fundus measuring apparatus related to any one of aspects (1) to (8), wherein the wavelength of the illumination light beam 11 from the illumination light source is tunable or the illumination optical system 10 or the light receiving optical system 20 has a wavelength selective filter 32.

Here, when the illumination optical system 10 has a wavelength selective filter 32, the wavelength selective filter 32 is used instead of, for example, the spectral characteristic correcting filter 13. With this constitution, a series of photographed images can be obtained at wavelength intervals of, for example, 10 nm.

To solve the above problem, a spectroscopic fundus measuring method, related to aspect (10) of the present invention comprises, as shown in FIG. 4 for example, a step (S001) of illuminating a fundus of a subject eye of an animal with a light beam from an illumination light source 11 emitting a light beam in a specified wavelength range; a step (S002) of photographing a series of spectral images of the fundus of the animal of different wavelengths by receiving a wavelength-tunable light beam reflected from the illuminated fundus; an image processing step of processing the spectral fundus images; and a storing step (S004) of storing the spectral fundus images, wherein the image processing step has a position correcting step (S003) of correcting the series of spectral fundus images photographed in the photographing step to match the positions of the same parts therein, and an image analyzing step (S005) of calculating the spectral characteristic of each part in the spectral fundus images based on the series of spectral fundus images corrected in the position correcting step; wherein the spectral characteristics of the parts are stored (S006) together with standard spectral characteristics of specific parts in the storing step, and wherein the image processing step has a first grouping step (S007) of comparing the spectral characteristic of each part with the standard spectral characteristics of the specific parts to divide the parts into groups corresponding to the specific parts.

With the above constitution, there can be provided a spectroscopic fundus measuring method capable of identifying each part in spectral fundus images easily and accurately based on its spectral characteristic. Here, the animal includes humans and living creatures other than humans.

To solve the above problem, a spectroscopic fundus measuring method related to aspect (11) comprises, as shown in FIG. 13 for example, a step (S001) of illuminating a fundus of a subject eye of an animal with a light beam from an illumination light source emitting a light beam in a specified wavelength range; a step (S002) of photographing a series of spectral images of the fundus of the animal of different wavelengths by receiving a wavelength-tunable light beam reflected from the illuminated fundus; an image processing step of processing the spectral fundus images; and a storing step (S004) of storing the spectral fundus images, wherein the image processing step has a position correcting step (S003) of correcting the series of spectral fundus images photographed in the photographing step to match the positions of the same parts therein, and a second grouping step (S007A) of regarding each principal component image formed by a principal component analysis method as a fundus image of a specific part (that is, regarding data corresponding to specific parts having a common spectral characteristic as being reflected in the n-th order principal component data) based on the series of spectral fundus images corrected in the position correction step to divide parts in the spectral fundus images into groups corresponding to the specific parts.

With the above constitution, there can be provided a spectroscopic fundus measuring method capable of identifying each part in spectral fundus images easily and accurately based on principal component analysis. As for the animal, the same as aspect (10) applies.

The invention related to aspect (12) is the spectroscopic fundus measuring method related to aspect (10) or (11), as shown in FIG. 4 or FIG. 13 for example, wherein the image processing step has a specific part image forming step (S008) of collecting respectively the parts divided into groups in the first grouping step (S007) or the second grouping step (S007A) to form images of the specific parts, and an image synthesizing step (S010) of synthesizing the images of the specific parts to form a synthesized fundus image.

With this constitution, fundus images regarding the specific parts can be efficiently formed using spectroscopic analysis or principal component analysis.

According to the present invention, there can be provided a spectroscopic fundus measuring apparatus capable of identifying each part in spectral fundus images based on its spectral characteristic easily and accurately and a measuring method therefor.

This application is based on the Patent Applications No. 2006-166691 filed on Jun. 15, 2006 in Japan, the contents of which are hereby incorporated in its entirety by reference into the present application, as part thereof.

The present invention will become more fully understood from the detailed description given hereinbelow. However, the detailed description and the specific embodiment are illustrated of desired embodiments of the present invention and are described only for the purpose of explanation. Various changes and modifications will be apparent to those ordinary skilled in the art on the basis of the detailed description.

The applicant has no intention to give to public any disclosed embodiment. Among the disclosed changes and modifications, those which may not literally fall within the scope of the patent claims constitute, therefore, a part of the present invention in the sense of doctrine of equivalents.

The use of the terms "a" and "an" and "the" and similar referents in the context of describing the invention (especially in the context of the following claims) are to be construed to cover both the singular and the plural, unless otherwise indicated herein or clearly contradicted by context. The use of any and all examples, or exemplary language (e.g., "such as") provided herein, is intended merely to better illuminate the invention and does not pose a limitation on the scope of the invention unless otherwise claimed.

DETAILED DESCRIPTION OF THE PREFERRED EMBODIMENT

Embodiments of the present invention are described below in reference to the drawings.

First Embodiment

Figure 1:
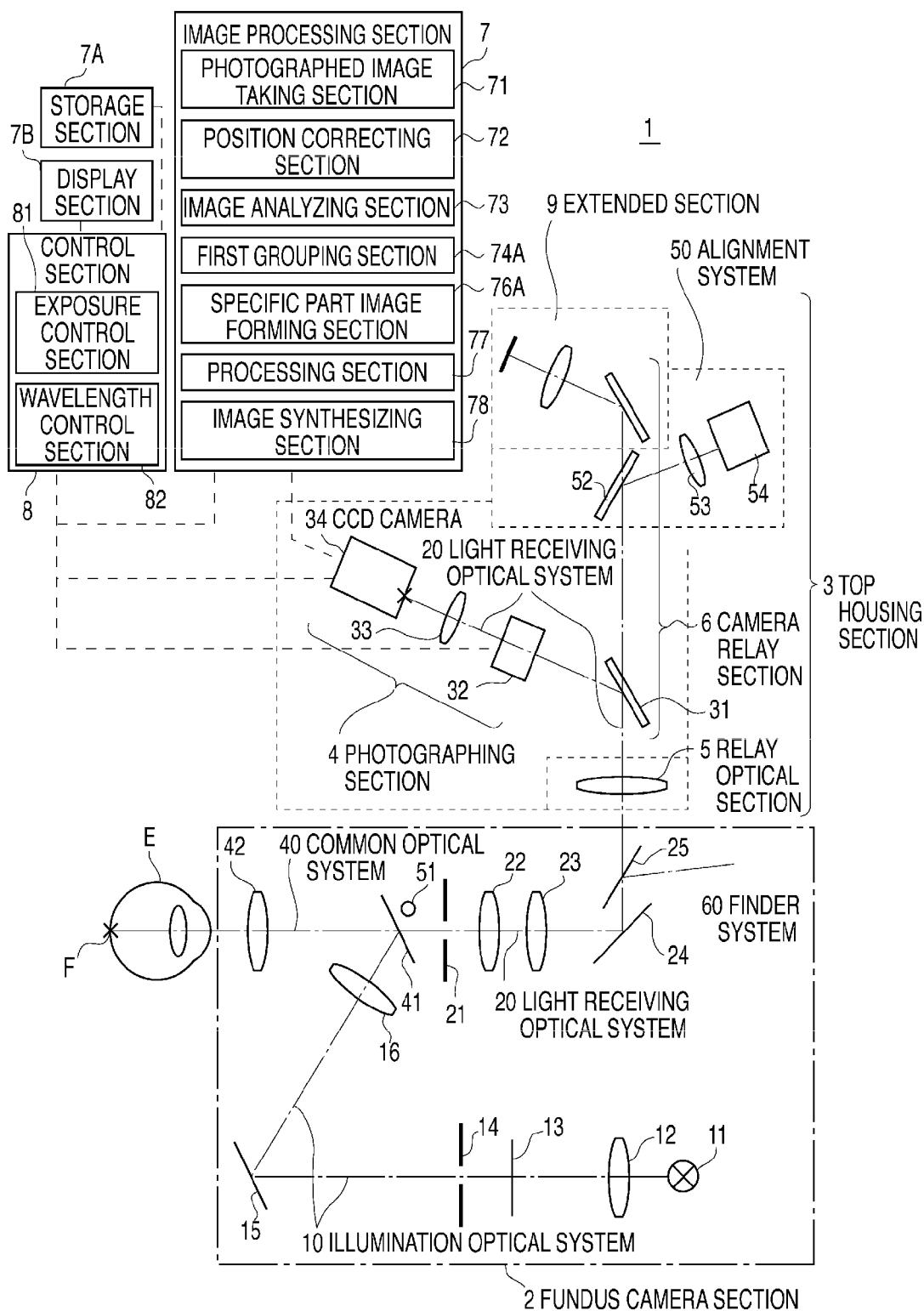
FIG. 1 shows an example constitution of a spectral fundus image measuring apparatus of a first embodiment.

FIG. 1 shows a general example of an optical system of a spectral fundus image data measuring apparatus 1 as an embodiment of the invention. In the drawing, the spectral fundus image data measuring apparatus 1 may be roughly divided into: a fundus camera section 2, a top housing section 3, an image processing section 7, a storage section 7A, a display section 7B, and a control section 8. The fundus camera section 2 comprises: an illumination optical system 10 for illuminating the fundus F of a subject eye E, the fore stage section of a light receiving optical system 20 for receiving light beam reflected from the fundus F and forming a fundus image on the light receiving surface of a photographing section 4, a finder optical system 60 for an optometrist to observe the fundus F, etc. The top housing section 3 is made up of the photographing section 4 for photographing a spectral fundus image, an alignment optical system 50 for aligning the illumination position of the illumination light on the fundus F (a light source 51 is provided at the fundus camera section 2), a relay optical section 5 for collimating the reflected light beam received from the fundus camera section 2 and leading it to a camera relay section 6, and the camera relay section 6 for transmitting the reflected light beam having passed through the relay optical section 5 to various light receiving means such as the photographing section 4 and comprises a hinder stage section of the light receiving optical system 20. The hinder stage section of the light receiving optical system 20 is made up of the relay optical section 5, the camera relay section 6, and the photographing section 4. An extended section 9 above the camera relay section 6 is a section for extended use by connecting various light receiving means such as a monitor TV, a hard copier, etc. to the light receiving optical system 20.

In the fundus camera section 2, the illumination optical system 10 is made up by disposing successively on its illumination optical axis: a halogen lamp 11 as an illumination light source, a condenser lens 12, a spectral characteristic correcting filter 13, a diaphragm 14, a mirror 15, a relay lens 16, and a beam splitter 41. Here, the halogen lamp 11 is placed near the front focal point of the condenser lens 12 and emits a wide wavelength range of light beam. The diaphragm 14 is disposed in a position to be conjugate with respect to the beam splitter 41.

The illumination optical system 10 further leads the light beam reflected from the beam splitter 41 through an objective lens 42 to illuminate the fundus F of the subject eye E. The area from the beam splitter 41 to the subject eye E constitutes an optical system 40 common to the illumination optical system 10 and light receiving optical system 20.

The light receiving optical system 20 is made up by disposing successively on the reflected light optical axis passing through the subject eye E: the objective lens 42, the beam splitter 41, an iris diaphragm 21, a focusing lens 22, an image forming lens 23, a mirror 24, a switching mirror 25; and is connected to the light receiving optical system of the top housing section 3. The iris diaphragm 21 is disposed in a position to be conjugate with the fore-end part of the subject eye E. When spectral images are to be taken, the switching mirror 25 is removed from the optical path, with for example a solenoid.

The alignment optical system 50 is to align the illumination light with the illuminated position on the fundus F, and is made up of a dichroic mirror 52, an image forming lens 53, and a monitoring camera 54, to observe reflected light when light is cast from the alignment light source 51 (provided in the fundus camera section 2) to the eye. The wavelength of the alignment light source 51 is set to be near infrared (for example 940 nm) so that alignment may be carried out without affecting the spectral images in the visible light range even when spectral images are being taken. The dichroic mirror 52 allows visible light (for example 750 nm or shorter in wavelength) to pass through and reflects light of longer wavelengths. The monitoring camera 54 may be for example a CCD camera. The finder optical system 60 is for an optometrist to observe the fundus F with the unaided eye. When the dichroic mirror 31 is used as a switching mirror and removed with for example a solenoid when spectral images are not being taken, it is possible to observe the fundus in color with the extended section.

In the top housing section 3, the light receiving optical system 20 has the relay optical system 5 placed on the axis of light reflected from the subject eye E, so that the light beam reflected from the fundus F is led through the relay optical system 5 into the camera relay section 6. In the camera relay section 6, a dichroic mirror 31 is placed on the reflected light axis to reflect visible light (for example 750 nm or shorter in wavelength) and allows light on the longer wavelength side to pass through. The light beam reflected from the dichroic mirror 31 is led to the photographing section 4. In the photographing section 4 are placed on the axis of light reflected from the dichroic mirror 31: a liquid crystal wavelength tunable filter 32, an image forming lens 33, and a CCD camera 34 having a light receiving surface. The light receiving surface is disposed to be conjugate with respect to the fundus F of the subject eye E, so that the fundus images are formed on the light receiving surface. The image forming lens 33 is to relay the light coming out of the liquid crystal wavelength tunable filter 32 to the CCD camera. Using the liquid crystal wavelength tunable filter 32 makes it possible to easily choose any wavelength in the visible light range and so facilitate analysis of the spectral characteristics. With this constitution, the light receiving optical system can receive a wavelength-tunable light beam reflected from the illuminated fundus to photograph a series of spectral fundus images of different wavelengths.

The image processing section 7 has a photographed image taking section 71 for taking a series of spectral fundus images photographed by the CCD camera 34; a position correcting section 72 for correcting the series of spectral fundus images to match the positions of the same parts therein; an image analyzing section 73 for calculating the spectral characteristic of each part in the spectral fundus images and the contrast between the brightness of each part in the spectral fundus images and the brightness of its background based on the series of spectral fundus images corrected in the position correcting section 72; a first grouping section 74A for comparing the spectral characteristic of each of the parts with standard spectral characteristics of specific parts to divide the parts into groups corresponding to the specific parts; a specific part image forming section 76A for collecting the parts divided into groups for each specific part to form images of the specific parts; a processing section 77 for performing processing such as filtering, labeling, expanding and thinning a line on the fundus images; and an image synthesizing section 78 for synthesizing the images of the specific parts to form a synthesized fundus image, and stores programs for image position matching correction flow, fundus image analysis flow, grouping flow, specific part image formation flow, image processing flow, and so on.

The storage section 7A stores the series of spectral fundus images photographed and corrected, various fundus images such as connected, synthesized and processed fundus images, spectral characteristics and contrasts calculated based on the series of spectral fundus images, and so on. The display section 7B displays on a screen the above various fundus images, spectral characteristics, contrasts and so on.

The control section 8 controls the entire spectral fundus image measuring apparatus 1, where the objects to be controlled include actions of the fundus camera section 2, the top housing section 3, the image processing section 7, the storage section 7A, and the display section 7B, and the flow of data and signals, in order to measure spectral fundus image data. It also has an exposure control section 81 for controlling the exposure of the CCD camera 34 and a wavelength control section 82 for controlling the transmission wavelength and so on of the liquid crystal wavelength tunable filter 32, and stores programs for the flow of taking spectral fundus images and the flow of setting exposure time for the CCD camera. Incidentally, the image processing section 7 and the control section 8 may be embodied with an ordinary personal computer.

Next is described the spectral characteristic of the optical system of the spectroscopic fundus measuring apparatus of the embodiment. For the analysis of the spectral characteristics, mainly a wavelength range of 430 to 950 nm is used, within which as uniform a spectral characteristic as possible is preferable. The received light intensity can be adjusted to be within the dynamic range of the CCD camera 34 with the CCD camera 34, the liquid crystal wavelength tunable filter 32, the correction filter 13, and the halogen lamp 11 (see Japanese Patent Application 2004-352093). In this embodiment, a dispersion-type light separating method is employed as a light separation method. While the Fourier-type light separation method can be named as one other than the dispersion-type light separation method, the dispersion-type light separation method is employed because of concern about noise on the images of a retina with the Fourier-type light separation method that uses interference. Incidentally, the Fourier light separation method may alternatively be used because it can separate light instantaneously and may be sometimes advantageous in terms of the amount of light. The reasons for using a halogen lamp as the illumination light source 11 are that it emits light over a wide range of wavelength from visible light to near infrared rays, that continuous lighting for about 10 seconds is required to separate light in time sequence, and that improvement on CCDs has made it possible to take images without using a flash.

The CCD camera 34 has sensitivity over a wide range of wavelength from visible light to near infrared range, and is capable of obtaining high-definition images for example of 1,300,000 pixels (1344×1024) and of reading at a high speed (about 8 frames/sec) with low noise. The exposure control section 81 of the control section 8 adjusts the exposure time of the CCD camera 34 in order to keep the light amount received to photograph CCD images constant. When the contrast of the CCD photographed images is not sufficient, the contrast may be improved by increasing the illumination light amount of the fundus illumination light source 11 or increasing the exposure time of the CCD camera 34.

Figure 2:
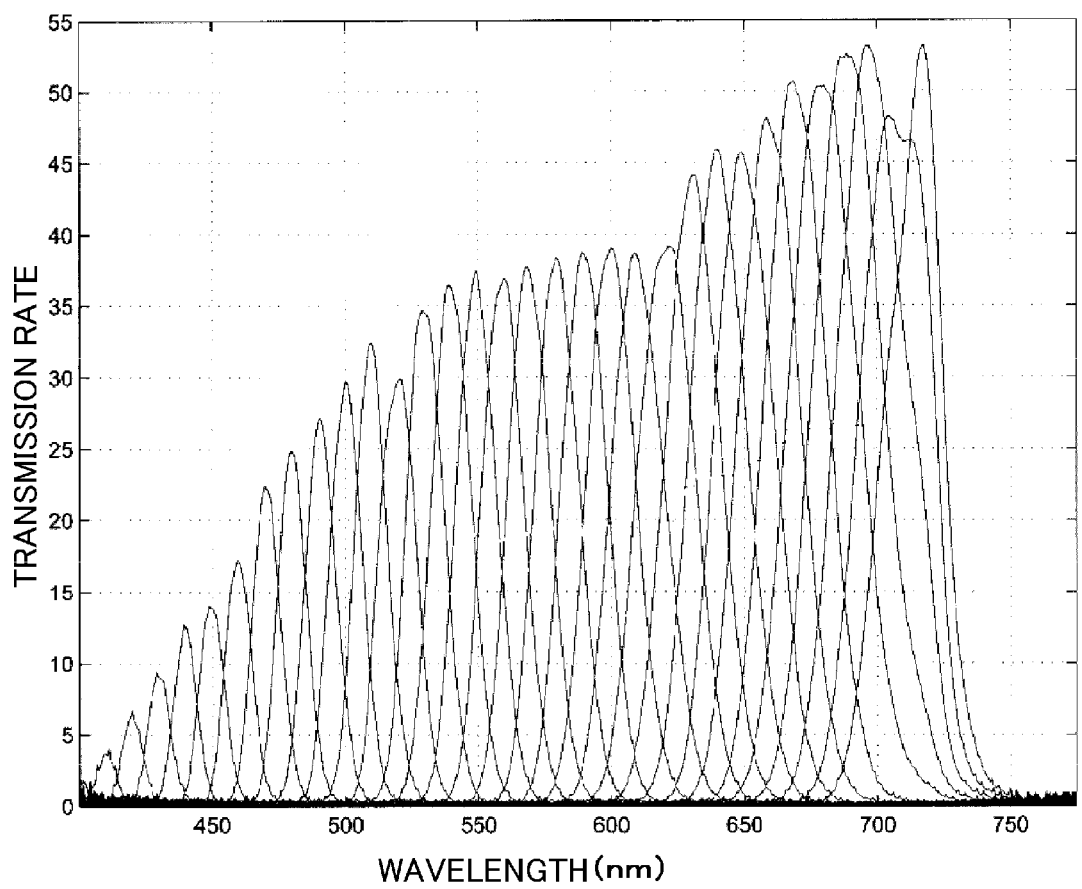
FIG. 2 shows an example of band-pass characteristic of a liquid crystal wavelength tunable filter.

FIG. 2 shows an example of band-pass characteristic of the liquid crystal wavelength tunable filter 32. The horizontal axis represents wavelength (nm) and the vertical axis transmission rate (%). As for the liquid crystal wavelength tunable filter 32, its transmission wavelength may be chosen in the range from 400 to 720 nm by changing the voltage applied to the liquid crystal. The drawing shows how the transmission light changes when the transmission center wavelength is changed at 10 nm intervals. The wavelength width of the transmission light is about 20 nm. The peak value of the transmission light increases approximately monotonically with the increase in the wavelength.

Figure 3A:
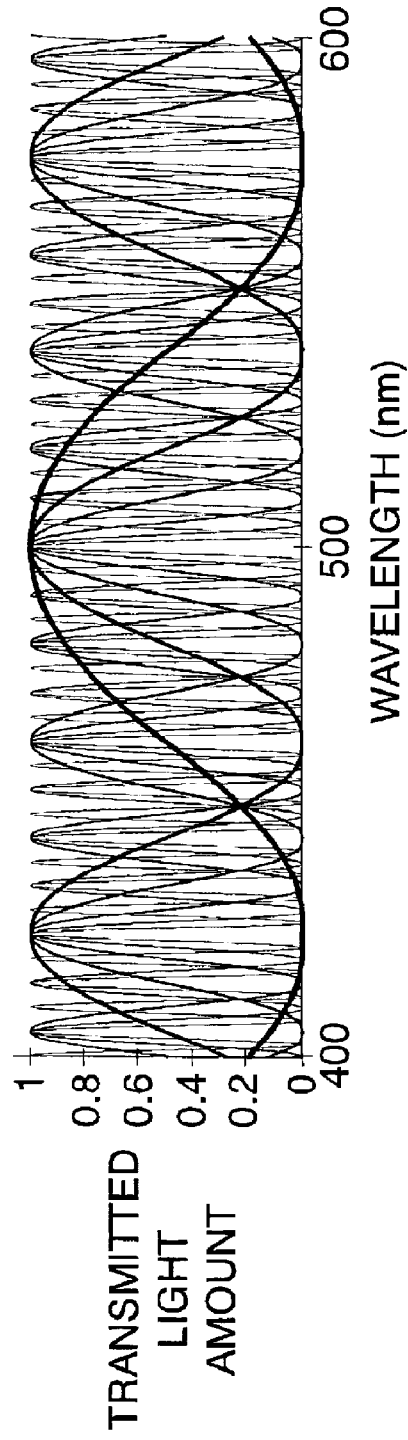
FIG. 3A and FIG. 3B show an example of a method for choosing the wavelength of the liquid crystal wavelength tunable filter.
Figure 3B:
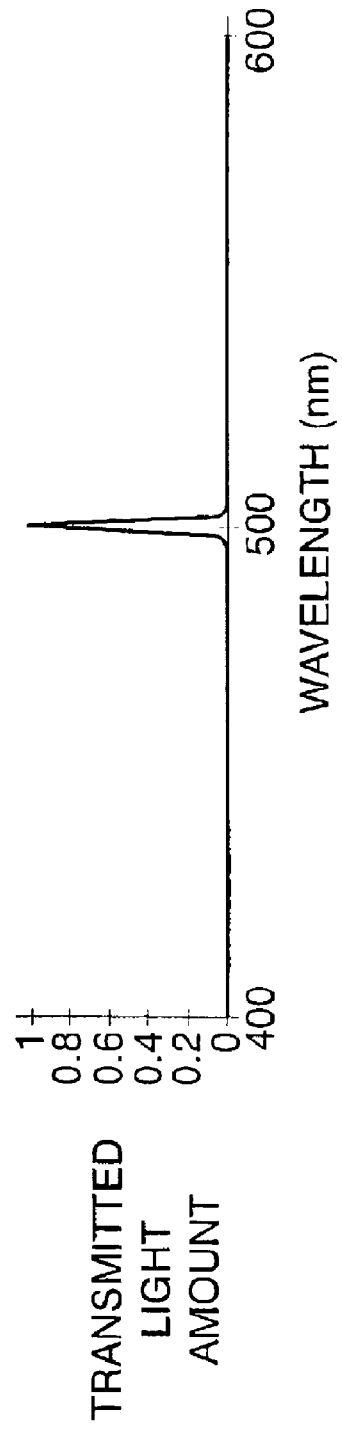

FIG. 3A and FIG. 3B show an example of wavelength choosing method with the liquid crystal wavelength tunable filter 32. Wavelength plates of different thicknesses are combined to narrow the output wavelength width, and the combinations are stacked in several stages (six stages for the example shown) to realize a wavelength width of 20 nm. FIG. 3A shows the filter characteristic of each of the Liquid Crystal Tunable Filters (LCTF) superposed in six stages. FIG. 3B shows the filter characteristic of the liquid crystal wavelength tunable filter 32 made by superposing six stages of the LCTFs. In both of the drawings, the horizontal axis represents wavelength (nm), and the vertical axis transmission rate. The transmission center wavelength may be arbitrarily changed quickly by changing the voltage applied to each LCTF, so that light of any intended wavelength component may be extracted.

Incidentally, since the liquid crystal wavelength tunable filter 32 is affected with the direction of polarization of the incident light, alignment appropriate for the polarization angle of the incident light is required when polarized light is used. In that case, the light emerging out of the liquid crystal wavelength tunable filter 32 is maintained in the same direction of polarization as the incident light.

[Process Flow of Spectral Fundus Measuring Method]

Figure 4:
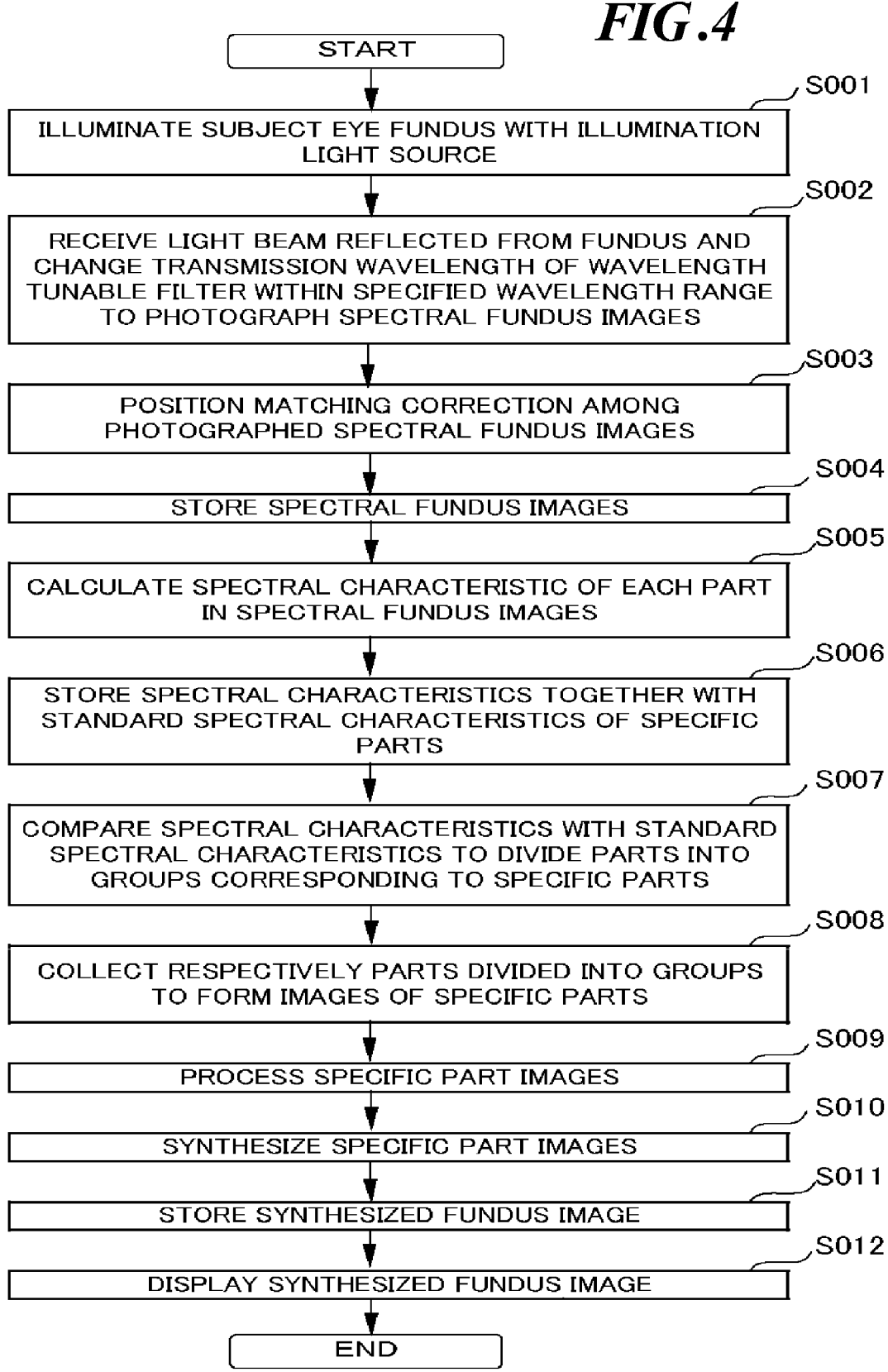
FIG. 4 shows an example flow of a spectral fundus image data measuring method of the first embodiment.

FIG. 4 shows an example process flow of a spectroscopic fundus measuring method of this embodiment. First, the fundus of a subject eye is illuminated with the illumination light source 11 (S001: subject eye illuminating step). The photographed image taking section 71 receives the illumination light beam reflected from the fundus and changes the transmission wavelength of the wavelength tunable filter 32 within a specified wavelength range to acquire photographed images of the spectral fundus image (S002: photographing step). The photographed images are acquired in succession from, for example, the short wavelength side. Next, the position correcting section 72 corrects the series of photographed spectral fundus images to match the positions of the same parts therein (S003: position correcting step). The series of corrected spectral fundus images are stored in the storage section 7A together with the series of photographed spectral fundus images (S004: first storing step). Next, the spectral characteristic of each part in the spectral fundus images is calculated based on the series of corrected spectral fundus images (S005: spectral characteristic analyzing step), and stored in the storage section 7A together with standard spectral characteristics of specific parts (S006: second storing step). Next, the parts are divided into groups based on the series of corrected spectral fundus images (S007: grouping step). As methods of grouping, there are (a) method in which the spectral characteristics are observed, (b) method using principal component analysis, etc. That is, parts with similar spectral characteristics (parts correlated with each other) are classified into one group. In this embodiment, the method in which the spectral characteristics are observed is employed. That is, the spectral characteristic of each of the parts is compared with standard spectral characteristics of specific parts to divide the parts into groups corresponding to the specific parts. Next, the parts divided into the groups are respectively collected to form images of the specific parts (S008: specific part image forming step). Next, the processing section 77 performs processing such as noise removal on the specific part images (S009: processing step). Next, the image synthesizing section 78 synthesizes the fundus images processed for respective specific parts to form a high-contrast synthesized fundus image (S010: image synthesizing step). The formed high-contrast synthesized fundus image is stored in the storage section 7A (S011: third storing step), and displayed on the display section 7B (S012: displaying step).

[Position Correction (Registration)]

The subject of measurement is a patient in a medical site, and it is preferred that the patient can be subjected to the measurement as comfortably as possible. In this embodiment, the measurement can be made without irradiating the fundus of a patient with strong light of a flash although the measurement takes a little longer time than the measurement with an ordinary fundus camera. However, there is a possibility that the fundus image is shifted to some extent by the influence of eye motion and so on within 20 seconds, in spite of comfortableness for a patient. The present inventors therefore developed a technique for matching the positions of a series of spectral fundus images of different wavelengths (registration technique). With it, spectroscopic analysis can be conducted even when the alignment state between an eye and the fundus camera is changed (see Japanese Patent Application 2004-352093).

Figure 5:
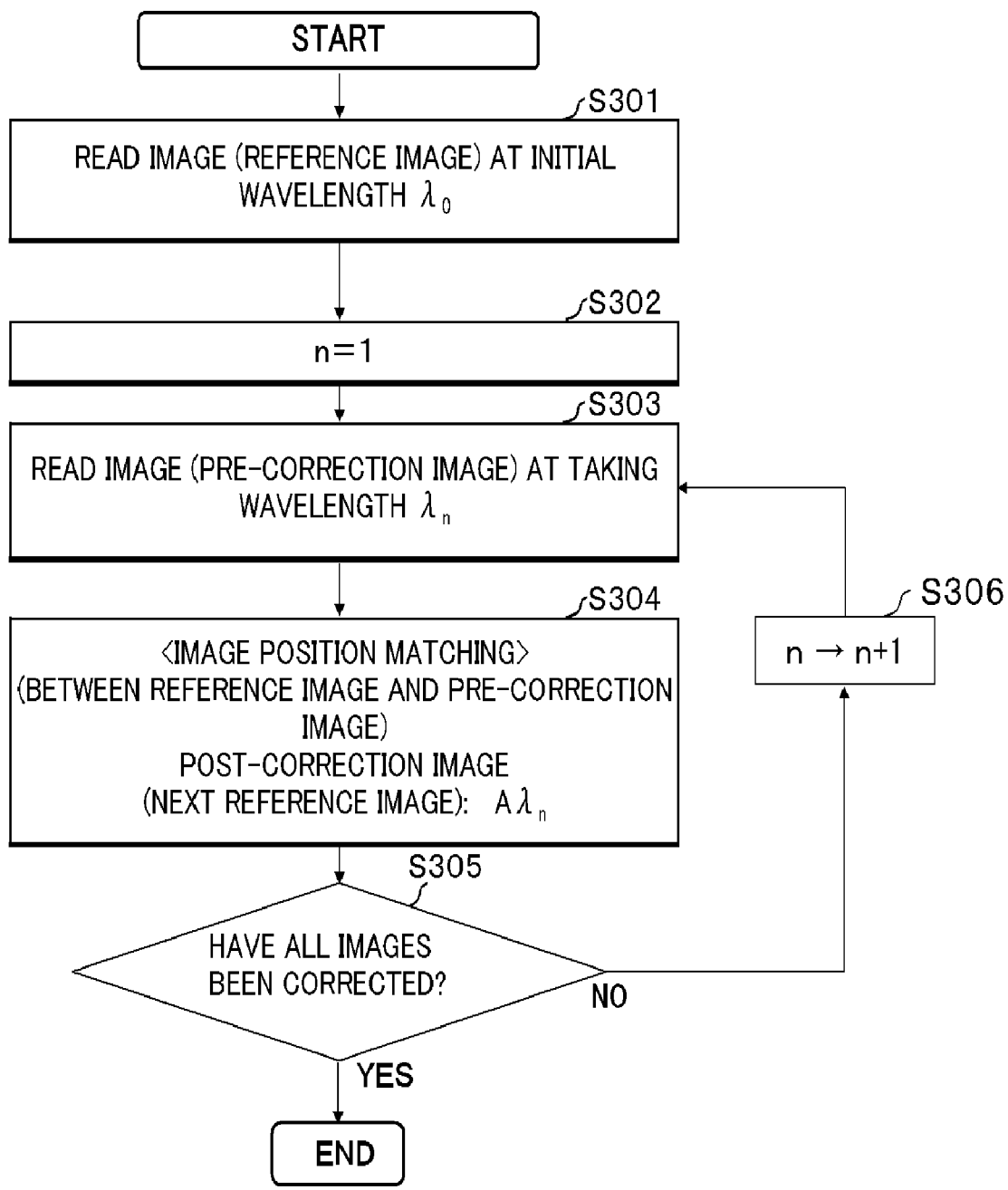
FIG. 5 shows an example flow of matching spectral retinal image positions.

FIG. 5 shows an example flow of matching spectral fundus image positions. This corresponds to the step S003 of FIG. 4. As for taking a series of spectral fundus images, photographing at 10 nm intervals from 500 nm to 720 nm currently takes about 20 seconds under conditions of wavelength tuning time of the liquid crystal wavelength tunable filter 32, the exposure time of the CCD camera 34, etc. During that time, in many cases, undesirable displacements occur in alignment between the subject eye E and the fundus camera section 2 and in stationary viewing. As a result, the position of the spectral fundus images taken is displaced, and a position on the fundus images corresponding to the same coordinates on the light receiving surface of the CCD camera 34 is displaced. Therefore, the position correction have to be performed. The correction is made by position matching among a series of spectral fundus images. Besides, the spectral fundus image changes with the change in the wavelength, and the change in the spectral image is recognizable even at a glance when the wavelength change is large. As a result, images, taken at wavelengths apart from each other, of the same part on the fundus, are hard to interrelate. Therefore in this embodiment, alignment is corrected with reduced error as follows: First, position matching is made between two images taken at the shortest and second shortest wavelengths. Next, position matching is made between the images taken at the second shortest and the third shortest wavelengths, like a chain reaction. This image position matching is made in the position correcting section 72 of the image processing section 7.

First, a photographed fundus image is read at an initial (shortest) wavelength $\lambda_0$ to start taking images, and the image read is assumed to be a reference image (step S301). Next, the number (n) of times of image position matching is set to one (step S302). A photographed fundus image as an object of position matching (next shortest in wavelength to the reference image, called an image at a taking wavelength $\lambda_n$) is read, and the image is assumed to be a pre-correction image (step S303). Then, position matching is done between the reference image and the pre-correction image to correct its position. The pre-correction image with its position corrected is now assumed to be a new reference image (step S304). If any image not corrected remains (NO in the step S305), n is incrementally increased (step S306), a fundus image photographed at the next taking wavelength $\lambda_n$ is read (step S303). The image position matching is repeated until the correction is made to all the photographed fundus images (YES in the step S305). Incidentally, reading the photographed fundus images in this flow may be re-reading the images already read into the storage section 7A by the image processing section 7 from the CCD camera 34 via the photographed image taking section 71, into the position correcting section 72. The flow of spectral fundus image position matching, including the loop process, may be controlled by a program. The program is stored in the image processing section 7, and the image position matching is carried out in the position correcting section 72.

Figure 6:
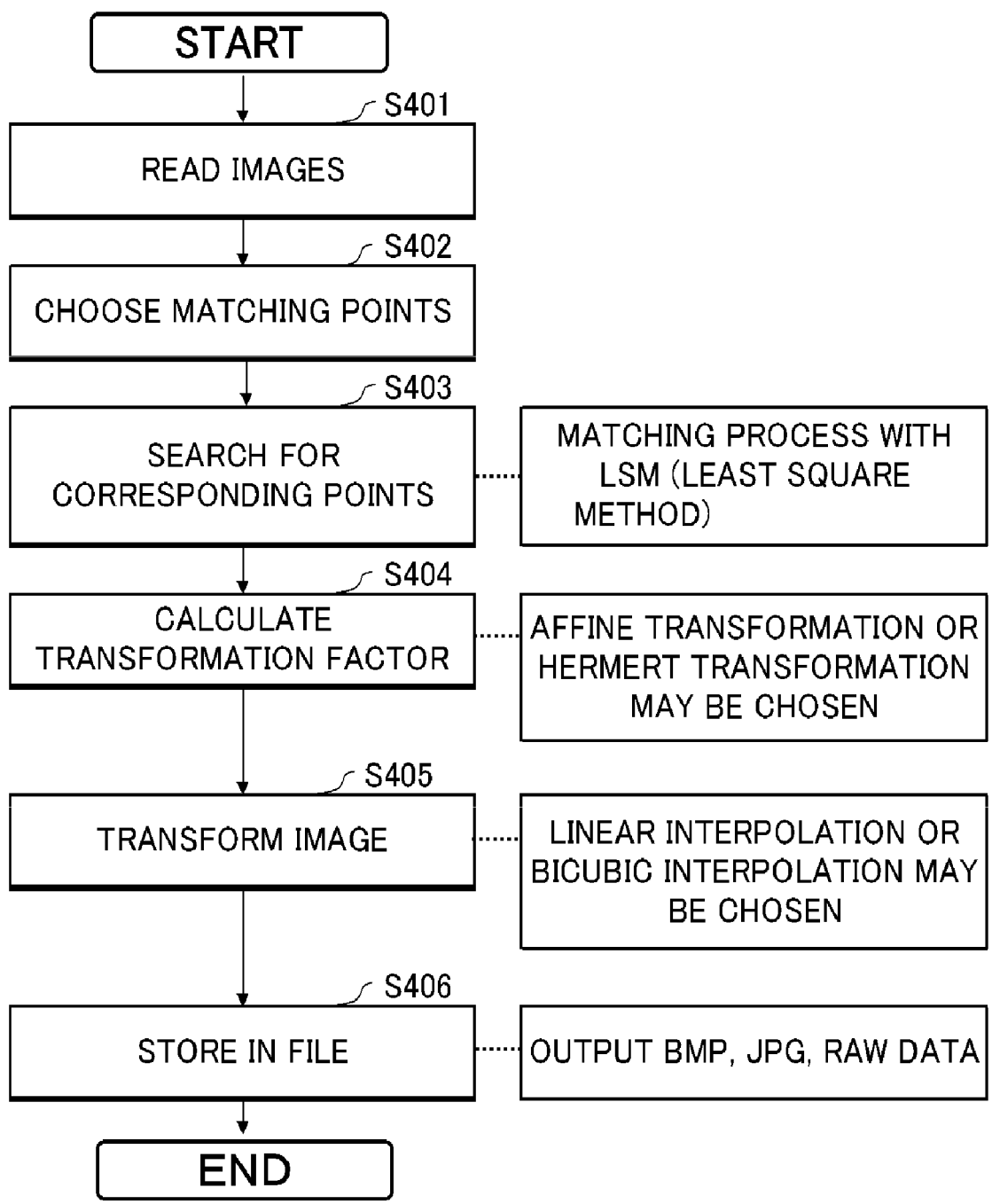
FIG. 6 shows an example flow of image position matching.

FIG. 6 shows an example flow of image position matching. It corresponds mostly to the step S304 of FIG. 5. Two spectral fundus images (reference image and pre-correction image (image taken at the adjacent wavelength)) of the illuminated fundus taken at different time points according to signals from the light receiving surface of the photographing section 4 are read (step S401) (This corresponds to the steps S301-S303 of FIG. 5. Steps S402 and after correspond to the step S304 of FIG. 5). Next, a plural number of characteristic points (points that are characteristic and highly conspicuous, may be linear in some cases) are chosen as image matching points from the two images (step S402). Next, positions of corresponding matching points are searched (step S403). For the search, for example the least squares matching (LSM) is used.

The least square matching is a method for performing the matching (to establish correlation) in which the position and shape of a template are fixed, and the position and shape of a matching window are changed so that the sum of the squares of the difference in shade becomes a minimum between the matching window and the template. For changing the position and shape of the matching window, the affine transformation or Hermert transformation may be chosen. As for these, difference in shade is calculated with varied transformation factors to determine the optimum factor (step S404). Next, transformation of the pre-correction image is carried out using the determined transformation factor (step S405). Here, a linear interpolation method or bicubic interpolation method may be chosen.

The bicubic method is a method for interpolating images and is called cubic interpolation method. As for the scanner in general, many models perform calculation with the primary interpolation method (calculation is made in reference to pixels on a straight line passing two points) or the nearest neighbor method. With the bicubic method, loss of information is the least, and in case of photographic images, the images obtained are smooth and natural. However, it takes much time because of complicated numerical operations. In contrast to the nearest neighbor method in which the value is determined from a single pixel in the neighborhood, the linear interpolation method determines the value from four pixels in the nearest neighborhood, so that interpolation accuracy is high in comparison with the nearest neighbor method.

Next, the image transformed from the pre-correction image is stored in a file (step S406). The stored image is used as a new reference image in the next image matching. The data may be stored for example in BMP format, in JPG format, or may be output as raw data.

[Image Analysis]

The images subjected to position matching by means of registration can be spectroscopically compared with one another. In this embodiment, the spectral characteristic of each part can be analyzed based on a series of spectral fundus images to determine wavelength ranges in which respective specific parts are clearly visible and to clarify whether each part belongs to any of the specific parts. In addition, the contrast between the brightness of each part and its background is calculated based on the series of spectral fundus images to contribute to the choice of images with maximum contrast.

Figure 7:
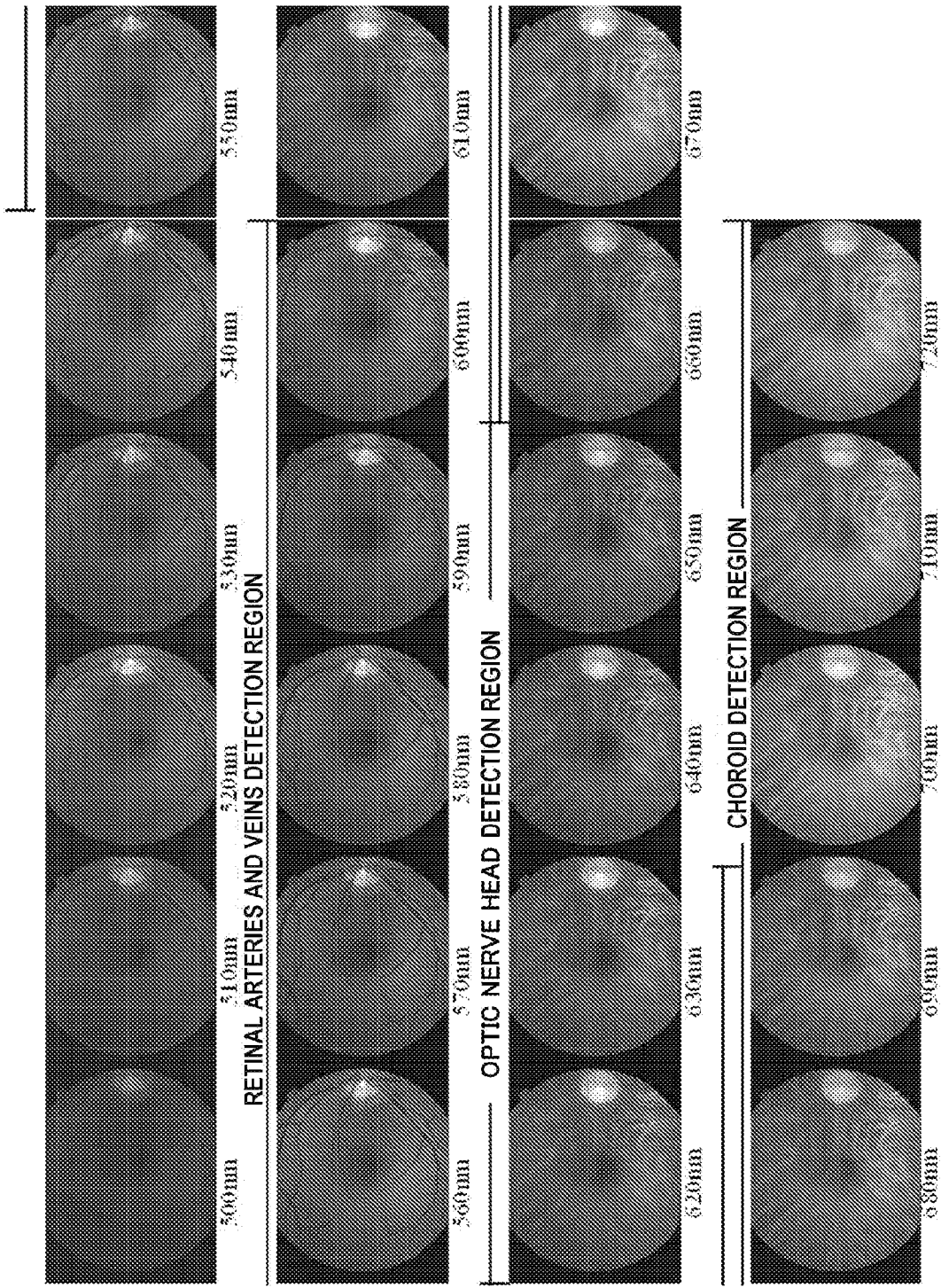
FIG. 7 shows an example of a hyperspectral image of spectral fundus images.

FIG. 7 shows an example of hyperspectral image, that is, a sequence of spectral fundus images of different wavelengths. When the images subjected to registration are arranged in the order of wavelength as shown in FIG. 7 and a pixel within the image plane is designated, the changes of reflected light at each wavelength can be known. The spectral characteristics based on the series of spectral fundus images of different wavelengths include information on the structural and physical features of each part of the fundus. The images are photographed at 10 nm wavelength intervals in the wavelength range from 500 nm to 720 nm. The retinal arteries and veins are visible relatively clearly in the wavelength range from 550 nm to 600 nm, and this range is called retinal arteries and veins detection region. The optic nerve head is visible relatively clearly in the wavelength range from 620 nm to 690 nm, and this range is called optic nerve head detection region. The choroid is visible relatively clearly in the wavelength range from 660 nm to 720 nm, and this range is called choroid detection region. These regions, in which clear images of respective specific parts can be obtained, may be determined by measuring the contrast or may be determined empirically by the visual sense. Therefore, when the retinal arteries and veins need to be observed, images in a wavelength range from 550 nm to 600 nm may be displayed. When the optic nerve head needs to be observed, images in a wavelength range from 620 nm to 690 nm may be displayed. When the choroid needs to be extracted, images in a wavelength range from 660 nm to 720 nm may be displayed. Each of the specific parts such as retinal arteries and veins, optic nerve head, choroid has its own spectral characteristic.

Figure 8:
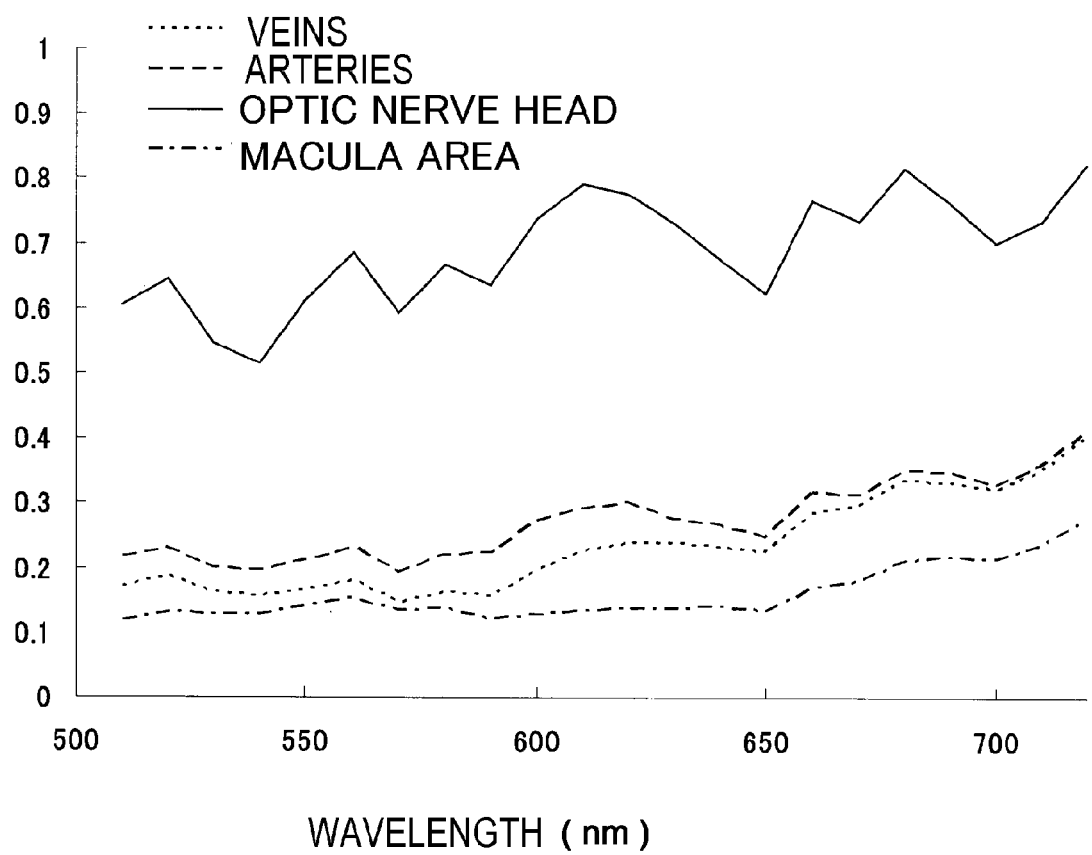
FIG. 8 shows an example of spectral characteristics of specific parts.

FIG. 8 shows an example of spectral characteristics of respective specific parts. The horizontal axis represents wavelength (nm) and the vertical axis represents received light intensity. The drawing shows the spectral characteristics of optic nerve head, retinal arteries, retinal veins and macula area. Optic nerve head exhibits by far the highest received light intensity among them, and retinal arteries, retinal veins and macula area exhibit relatively low received light intensities, decreasing in this order. In the reflection from the fundus, only the retina can be observed at a wavelength shorter than approximately 600 nm. At a wavelength longer than 600 nm, reflection from the choroid can be also observed. For example, when the fundus is photographed at 630 nm or 780 nm, an image of choroidal vessels can be obtained. Also, since the same part exhibits a similar spectral characteristic as shown in FIG. 8, each specific part can be identified based on the difference in spectral characteristic. In addition, the wavelength range in which a clear image can be obtained is different for each specific part. In other words, when an image is observed at a suitably chosen wavelength, the blood vessels in the choroid and the blood vessels in the retina, for example, can be distinguished.

[Grouping]

Figure 9:
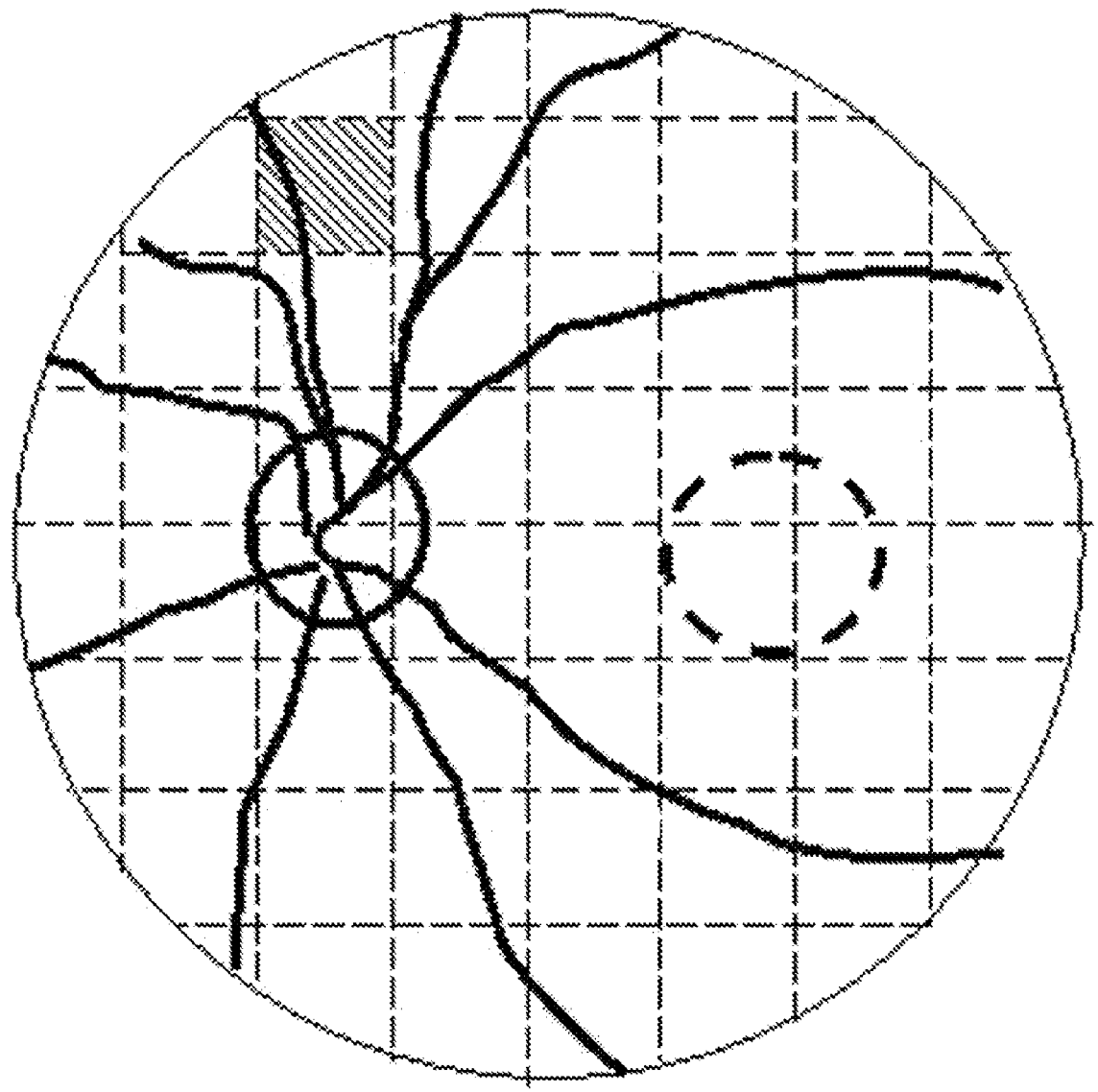
FIG. 9 shows an example of a fundus image including retinal arteries and veins and optic nerve head.

FIG. 9 explains the grouping of specific part groups. Grouping is to obtain the spectral characteristic of each part in the obtained spectral fundus images and divide the parts into groups of parts with similar spectral characteristics to identify the parts. In this embodiment, the spectral characteristic of each part is compared with standard spectral characteristics of specific parts to divide the parts into groups corresponding to the specific parts. The grouping process is automatically performed in the first grouping section 74A. Here, an example of retinal arteries and veins and optic nerve head is shown. In the drawing, the very bright elliptical area on the left side of the center corresponds to the optic nerve head, and the thin linear parts extending radially therefrom correspond to the retinal arteries and veins.

First, each spectral fundus image is divided into square areas, and the spectral characteristic of the part in each area is compared with a standard spectral characteristic of each specific part (retinal arteries and veins, optic nerve head, choroid, etc.) stored in the storage section 7A. When matching is achieved, the part is classified into a group as the specific part. In the example shown in FIG. 9, the parts are classified into groups of either retinal arteries and veins or optic nerve head for each area, and in some of the areas they are classified into two groups. Parts with a spectral characteristic which nearly matches but slightly differs from a standard spectral characteristic of a specific part because of deterioration in health or the like are classified into a group as parts which are close to the specific part but have abnormality. Parts which do not match any of the specific parts are classified into a group as others. The group of others may be classified into smaller groups by their patterns. Each part can be detected based on its characteristics. For example, the retinal arteries and veins are characterized by their linear shape and low brightness, the optic nerve head is characterized by its elliptical shape, and the choroidal vessels are characterized by their linear shape and high brightness, and they can be extracted based on these characteristics. It is preferred to detect them in the following order: the optic nerve head, which is easy to detect in terms of image processing, the retinal arteries and veins extending linearly from the optic nerve head, and the choroidal vessels.

Next, the contrast in each area is calculated at each wavelength:

$$(I_{max}-I_{min})/(I_{max}+I_{min})$$

($I_{max}$: maximum value of brightness, $I_{min}$: minimum value of brightness) Then, the image with the highest contrast in the wavelength range for each of the objects (retinal arteries and veins, optic nerve head, choroids, etc.) is obtained from the images of each area. That is, the image with the highest contrast is chosen from the images of each area in the images extracted from the retinal arteries and veins detection region ranging from 550 nm to 600 nm in the case of the retinal arteries and veins, from the optic nerve head detection region ranging from 620 nm to 690 nm in the case of the optic nerve head, from the choroid detection region ranging from 660 nm to 720 nm in the case of the choroid. Then, when the parts as objects of measurement are determined to belong to any of the specific parts, the images with the highest contrast are displayed.

Next, the specific part image forming section 76A connects the parts classified into groups respectively to form images of the specific parts. At this time, the images in the groups of the parts which are close to a specific part but have abnormality are also connected. These parts are preferably distinguished by different colors or the like.

Next, the processing section 77 performs processing such as noise removal on the connected images of the specific parts.

[Processing]

Figure 10:
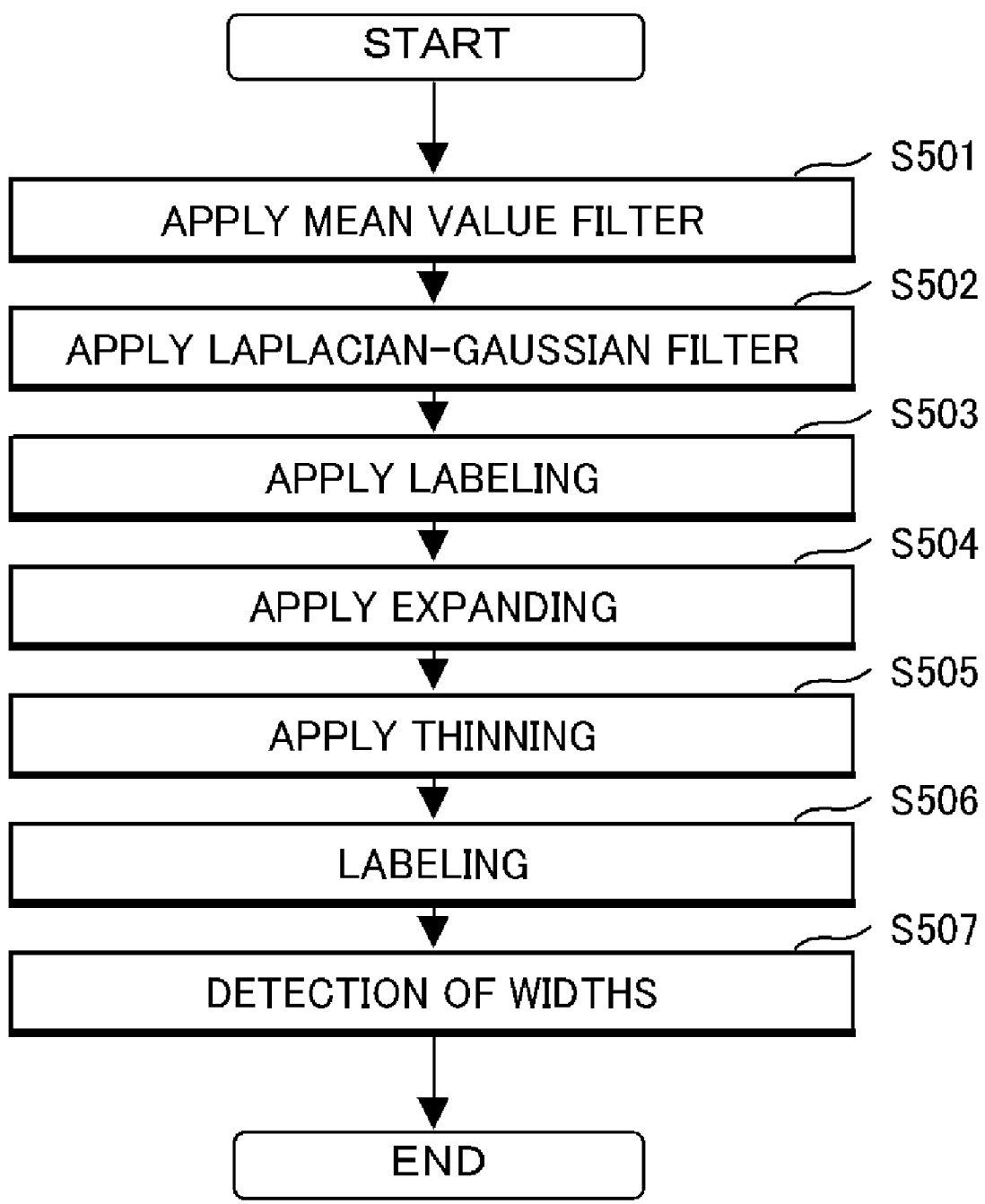
FIG. 10 shows the flow of image processing.
Figure 11:
FIG. 11 shows examples of images during the image processing.
Figure 11:
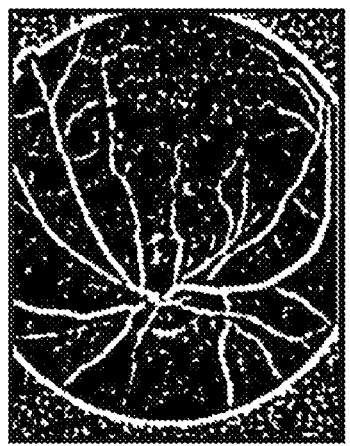
Figure 11:
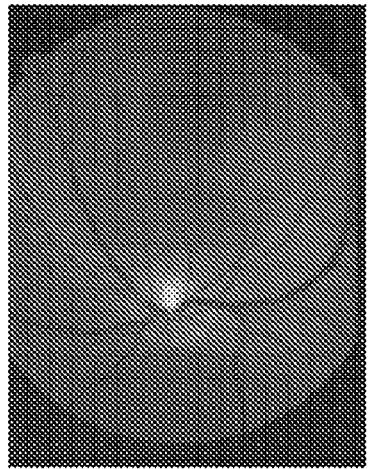
Figure 11:
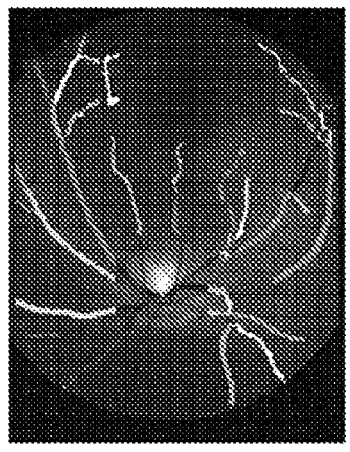

FIG. 10 shows the flow of processing, and FIG. 11 shows examples of images during the processing. The processing corresponds to S009 of FIG. 4. First, the connected image for each of specific parts is defined as an object image for detection (FIG. 11(a)). Here, the retinal arteries and veins are the objects of detection. First, a mean value filter is applied (S501), and then a Laplacian-Gaussian filter is applied (S502) (FIG. 11(b)). A mean value filter is an operator that averages pixels with their neighbors to remove noise, and a Laplacian-Gaussian filter is an operator that extracts edges with high contrast and applies a gaussian function to smooth them in order to remove noise. Next, labeling is carried out to give the same number to a series of parts with the same characteristic for identification (S503), expanding is carried out to expand points (S504), and thinning is carried out to reduce the width of lines in order to remove noise (S505) (FIG. 11(c)). Next, a label is attached, that is, an attribute is attached to each of the numbered parts, and, here, the parts are displayed in color (S506) (FIG. 11(d)). Next, the widths of the retinal arteries and veins are measured (S507). The widths are used as an index of health or medical condition. The processing is performed on the connected images for respective specific parts as described above to form clear fundus images without noise.

Next, the process returns to FIG. 4, and the image synthesizing section 78 synthesizes the fundus images processed for the chosen specific parts to form a high-contrast fundus image (S010). Colors are applied corresponding to the specific parts in the high-contrast fundus image, and the high-contrast fundus image is stored in the storage section 7A (S011). Then, the high-contrast fundus image is displayed in color on the display section 7B (S012).

As described above, according to this embodiment, there can be provided a spectroscopic fundus measuring apparatus capable of identifying each part in spectral fundus images based on its spectral characteristic easily and accurately and a measuring method therefor.

Second Embodiment

An example in which the spectral characteristic of each part is compared with standard spectral characteristics of specific parts to divide the parts into groups corresponding to the specific parts is described in the first embodiment. In the second embodiment, each principal component image formed by a principal component analysis method is regarded as a fundus image corresponding to a specific part based on the series of spectral fundus images corrected in the position correcting section to divide the parts in the spectral fundus images into groups corresponding to the specific parts.

Figure 12:
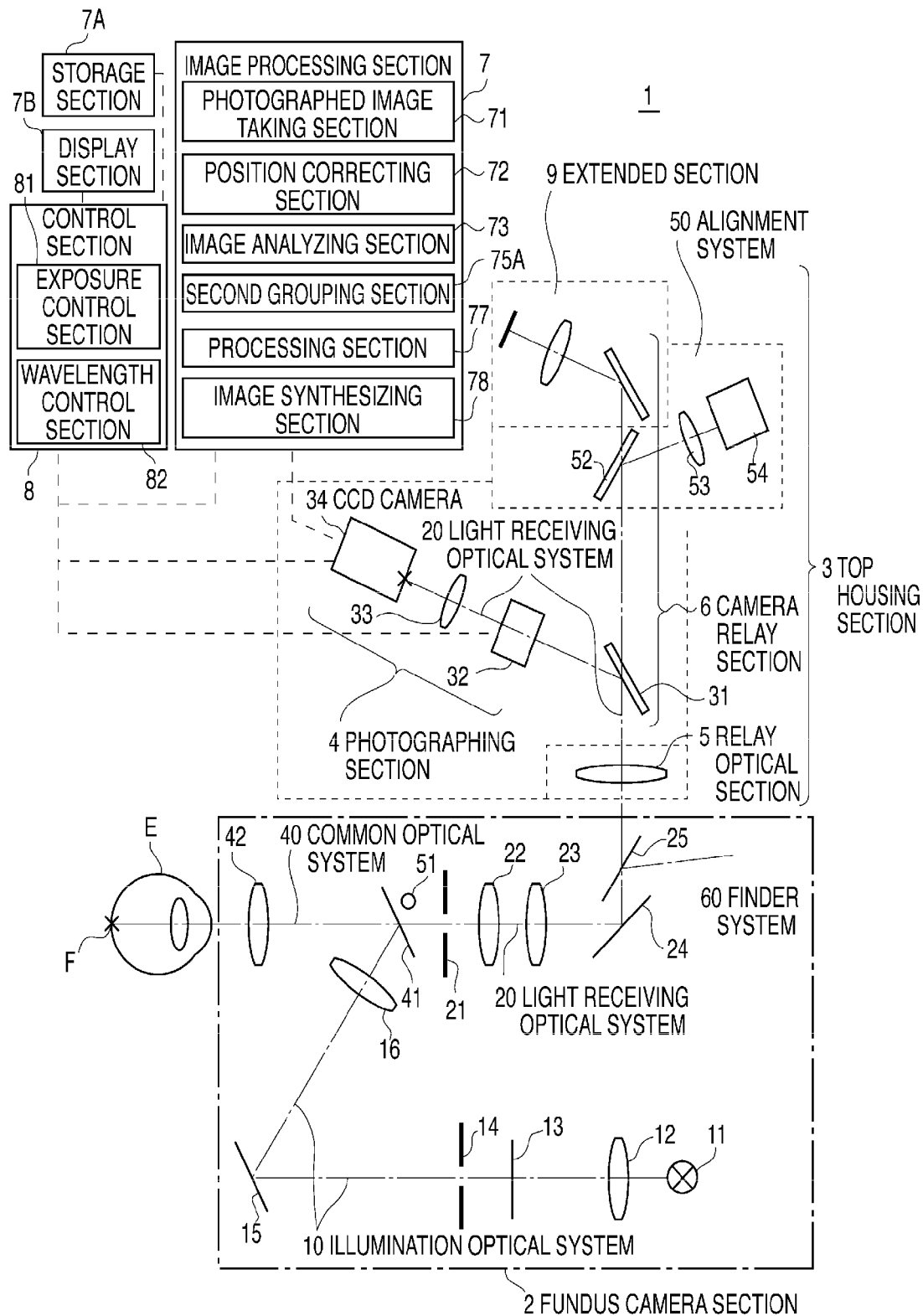
FIG. 12 shows an example constitution of a spectral fundus image measuring apparatus of a second embodiment.

FIG. 12 shows an example constitution of a spectral fundus image measuring apparatus of a second embodiment. The second embodiment is different from the first embodiment only in the grouping process. The difference is that the first grouping section 74A in FIG. 1 is replaced by a second grouping section 75A, and the specific part image forming section 76 can be omitted since specific part images are formed by the principal component analysis. The grouping is automatically performed in the second grouping section 75A.

Figure 13:
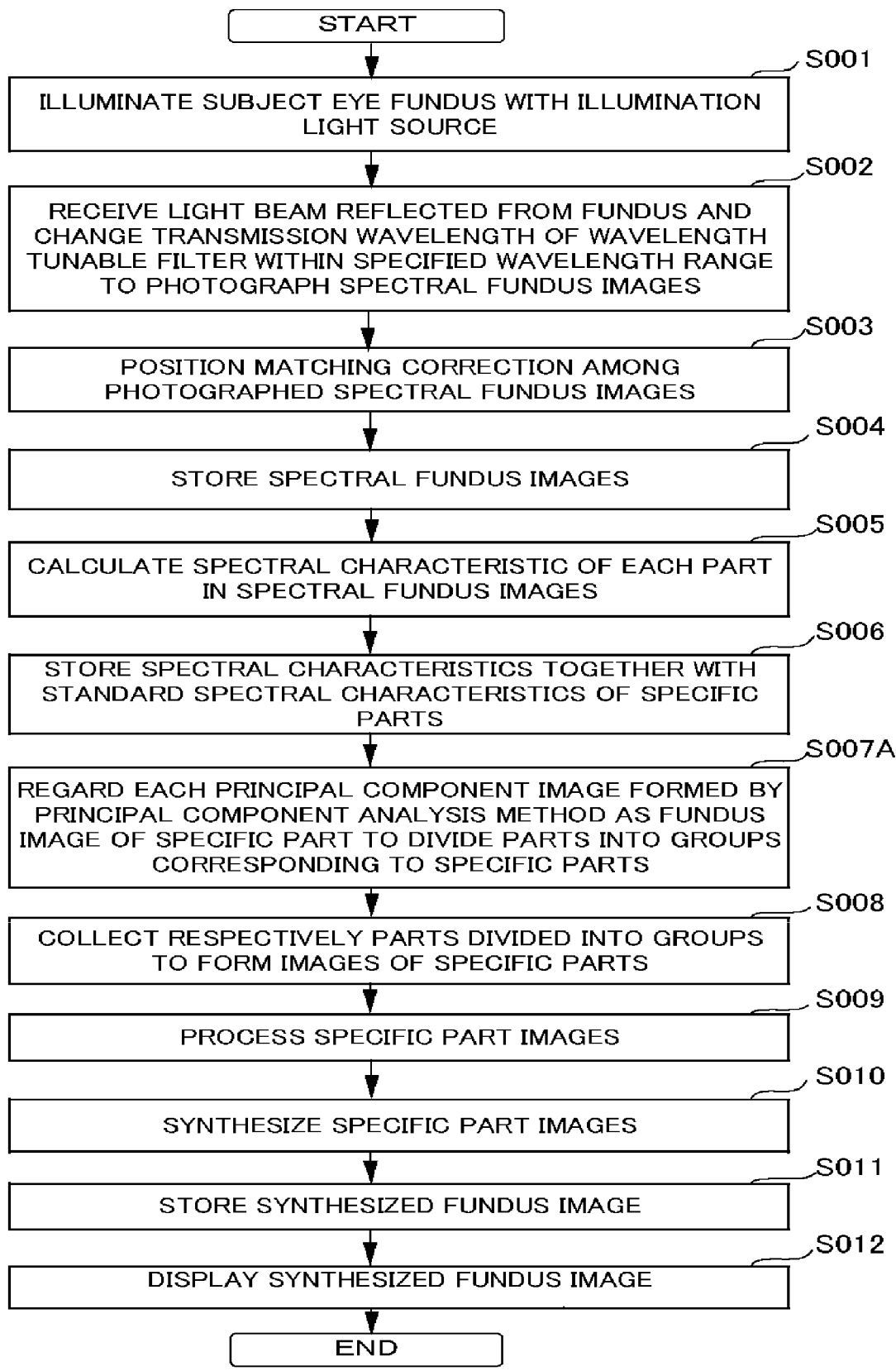
FIG. 13 shows an example flow of a spectral fundus image data measuring method of the second embodiment.

FIG. 13 shows an example flow of a spectral fundus image data measuring method of the second embodiment. The difference is that the first grouping step (S007) in the first embodiment shown in FIG. 4 is replaced by a second grouping step (S007A), and the specific part image forming step (S008) in FIG. 4, which is performed in the specific part forming section, is performed in the second grouping section. The second embodiment is the same in other respects as the first embodiment and has the same effect as the first embodiment.

[Principal Component Analysis]

In this embodiment, principal component analysis is employed as a method for finding the correlation between the parts in the spectral fundus images. That is, it is considered that the data corresponding to specific parts having a common spectral characteristic are reflected in the n-th order principal component data. The mathematical basis of the principal component analysis is presented below.

First, $a_j$ which maximizes the correlation between an original vector (which is a standard score here for the sake of convenience) and $f_j$ as a new principal component is obtained.

$$a_j = \left(\frac{1}{n}\right) Z' \frac{f_i}{s_{fj}}$$

$$= \frac{R\omega_j}{\sqrt{\omega_j' R \omega_j}} \quad (j = 1, \Lambda, r)$$

wherein $Z=(z_1, z_2, \Lambda, z_p)$, and $z_i$ is a standard score standardized to mean 1 and variance 1. Z' represents a transposed matrix of Z, and $\omega_j'$ represents a transposed matrix of $\omega_j$.

Also, $$f_j = \omega_{f1} z_1 + \omega_{f2} z_2 + \Lambda + \omega_{fp} z_p$$
$$= Z \omega_j$$

wherein $\omega_j$ is a weighing vector.
Also, $$s_{fj} = \sqrt{\frac{1}{n}(f_j, f_j)}$$

wherein $s_{fj}$ is a standard deviation of $f_j$.

Maximization of $a_j$ is equivalent to solving the following eigenvalue problem.

$$R a_j = \lambda a_j$$

The obtained proper vector and eigenvalue represent a principal component and the contribution rate of the principal component, respectively.

[Application of Principal Component Analysis to Image]

Suppose that there are N by M matrix images corresponding in number to K wavelengths, and all of them have been subjected to the registration described above.

First, it is assumed that an image of a wavelength (k) is represented as an ordinary two-dimensional array N×M. This is converted into a one-dimensional column vector. The algorithm below is expressed by a virtual language easy to understand.

```
Loop n from 0 to N−1
    Loop m from 0 to M−1
        IM1(n*M+m) = IM2(n,m)
    End Loop
End Loop
```

Next, a two-dimensional array as shown below is formed using all the images corresponding to the wavelengths to be analyzed.

$$Z = \begin{pmatrix} im_{0,0} & im_{0,1} & \ldots & \ldots & im_{0,K} \\ im_{1,0} & . & \ldots & \ldots & . \\ . & . & \ldots & \ldots & . \\ . & . & \ldots & \ldots & . \\ . & . & \ldots & \ldots & . \\ im_{N \times M, 0} & . & \ldots & \ldots & im_{N \times N, K} \end{pmatrix}$$

Usually, in the above array,
Number of rows >>Number of columns.

Thus, as a technique of calculation, correlations between images, not correlations between wavelengths, are obtained.

The array corresponds to Z in the principal component analysis. Here, standardization of the column vector (subtracting the mean value therefrom and dividing the result by the standard deviation/dividing by the standard deviation is not done in some cases), for example, is preferably performed in advance.

[Result of Analysis]

As a result of analysis, images corresponding to the principal components and the contribution rates of the components are outputted.

Figure 14:
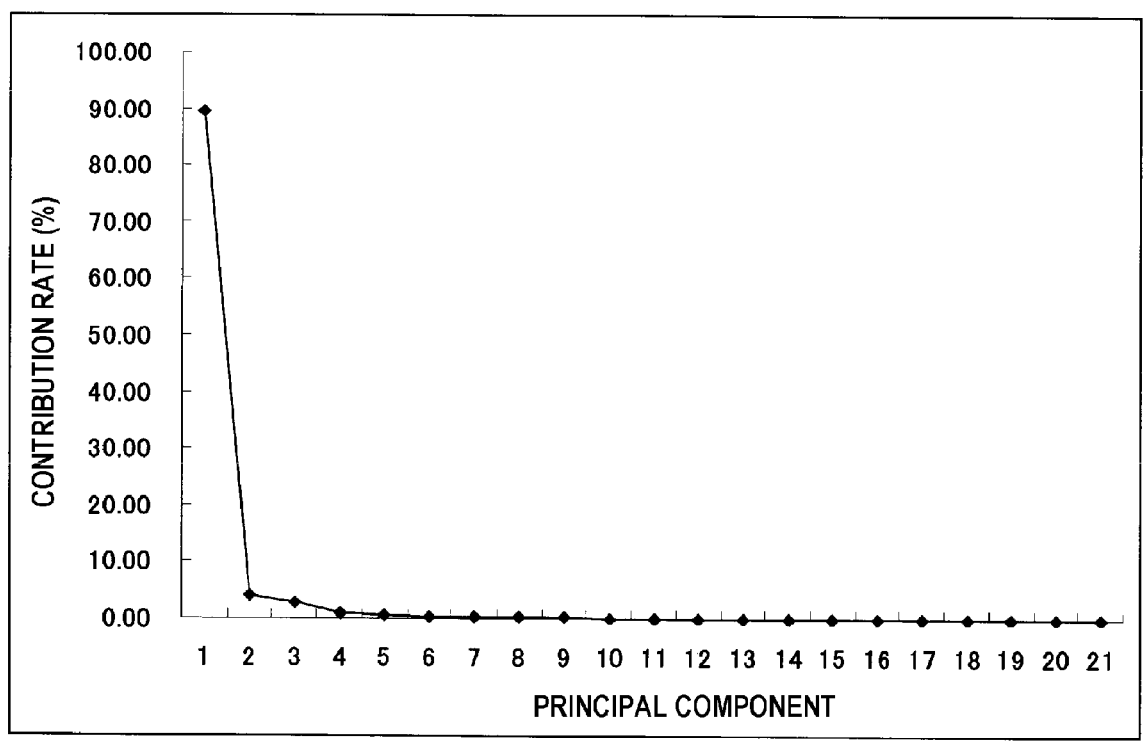
FIG. 14 shows an example of contribution rates of principal components.

FIG. 14 shows an example of contribution rates of principal components. The first principal component has a large contribution rate of approximately 90%. The contribution rates of second principal component to the fifth principal component are all 5% or less, decreasing in this order. The sixth and subsequent principal components have a contribution rate of almost 0%. As described above, some correlation can be extracted from the second to fifth principal components.

Figure 15:
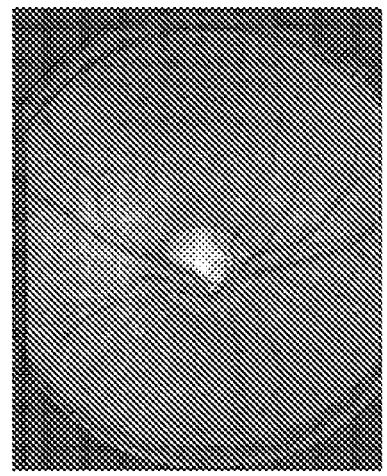
FIG. 15 shows examples of images corresponding to the principal components.
Figure 15:
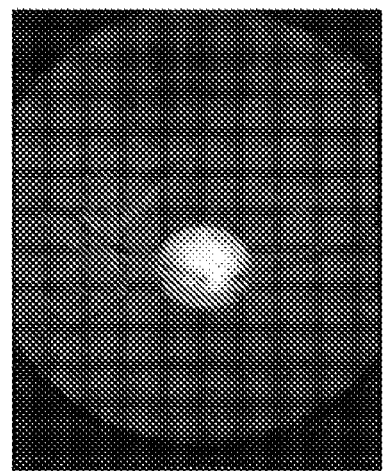
Figure 15:
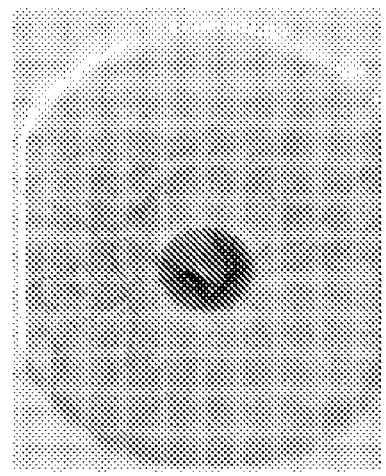

FIG. 15 shows images corresponding to principal components. In a first principal component PC1 (not shown), the basic shape of the retina appears as an image. The choroidal vessels appear in a second principal component PC2 shown in FIG. 15(a). The retinal veins appear in a third principal component PC3 shown in FIG. 15(b). The entire retinal blood vessels appear in a fifth principal component PC5 shown in FIG. 15(c). As above, a specific part on the fundus images is reflected in each principal component. In such a case, by removing the retinal vein component from the entire retinal blood vessel components, a retinal artery component can be obtained.

As described above, according to this embodiment, there can be provided a spectroscopic fundus measuring apparatus capable of identifying each part in spectral fundus images based on its spectral characteristic easily and accurately and a measuring method therefor.

Third Embodiment

An example in which the spectral fundus images are divided into relatively small areas and spectral characteristics are obtained from the areas and compared is described in the first embodiment. In the third embodiment, an example in which, as for long and thin parts such as retinal arteries and veins, spectral characteristics are obtained regarding one continuous vein and compared is shown. This embodiment is substantially the same as the first embodiment except for the size of the parts to be compared. The accuracy is lower but the processing can be carried out quickly since the number of parts to be compared is small.

Fourth Embodiment

An example in which the spectral characteristic of each part is compared with standard spectral characteristics of specific parts and the parts are automatically divided into groups is described in the first embodiment. In the fourth embodiment, an example in which the grouping is manually carried out. In this case, the image analyzing section 73 calculates the spectral characteristic of each part in the spectral fundus images based on the series of corrected spectral fundus images, and the storage section 7A stores the spectral characteristics of the parts together with the standard spectral characteristics of the specific parts. When the operator designates a part, the spectral characteristic of the part is displayed. The operator can compare the spectral characteristic with the standard spectral characteristics of specific parts to confirm that the part belongs to a specific part and classify the part into a group as the specific part. Also, the image analyzing section 73 calculates the contrast between the brightness of each part and the brightness of its background based on the series of corrected spectral fundus images, and the storage section 7A stores the contrasts of the parts. When the operator designates a part, the contrast of the part is displayed. The operator can refer the contrast when choosing images with high contrast to form images of the specific parts. The fourth embodiment is the same in other respects as the first embodiment and has the same effect as the first embodiment.

Fifth Embodiment

An example in which principal component analysis is automatically performed to carry out the grouping is described in the second embodiment. In the fifth embodiment, an example in which the grouping is manually carried out is shown. The result of principal component analysis is manually displayed, and the spectral characteristic and contrast of each part is displayed as in the fourth embodiment. Then, the operator checks the parts and divides them into groups. The operator can confirm with his/her own eyes when carrying out the grouping. The fifth embodiment is the same in other respects as the second embodiment and has the same effect as the second embodiment.

Sixth Embodiment

An example in which noise is removed by processing after the grouping is described in the first embodiment and the second embodiment. In the seventh embodiment, processing is performed on each of the corrected images. In this case, a multiplicity of images need processing but noise is removed from the data for the spectroscopic analysis and principal component analysis. Therefore, the reliability of the spectroscopic analysis and principal component analysis is improved. The sixth embodiment is the same in other respects as the first and second embodiments.

Seventh Embodiment

An example in which one set of the series of spectral fundus images are taken is described in the first and second embodiments. In the seventh embodiment, two sets of the series of spectral fundus images are taken so that the sets of the series of images can complement the position matching each other. That is, during 20 seconds of photographing, the spectral fundus image may be displaced. Thus, when the spectral fundus image is displaced relatively largely during photographing a first set of images, the position matching is carried out using images with less displacement in the other set and the images in the first set of images are converted to match them with the other set of the series of images. The position matching can be thereby carried out reliably. The seventh embodiment is the same in other respects as the first and second embodiments.

The present invention can be implemented as a program that enables a computer to perform the image processing method described in the above embodiments. The program may be stored in a memory incorporated in the control section 8, may be stored in a storage device provided inside or outside the system, or may be downloaded through the Internet. The present invention can be also implemented as a recording medium readable by a computer in which the program is stored.

While embodiments of the invention are described above, the invention is not limited to the above embodiments. Rather, it is apparent that the invention may be modified in various ways.

For example, while an example in which the images of specific parts are displayed on the display section was described in the above embodiments, the spectral fundus images are not necessarily displayed on the display section when the images of specific parts are automatically formed as in the second embodiment. Further, it is also possible to change the order of steps in the embodiments. For example, the fundus images may be stored at a time after taking spectral fundus images at all the wavelengths in the spectral measurement wavelength range, or each fundus image may be stored immediately after taking the spectral fundus image at each wavelength. Further, image position matching may be carried out successively while reading spectral fundus images (pre-correction images) from the CCD camera, or position matching among photographed images may be carried out successively, after reading into the photographed image taking section all the spectral fundus images from the CCD camera, while re-reading into the position correcting section the spectral fundus images (pre-correction images) accumulated in the storage section.

Further, while an example was described in which the programs for the spectral fundus image taking flow and the CCD camera exposure time setting flow are stored in the control section, and the programs for the spectral retinal image position matching flow, the spectral retinal image analysis flow and so on are stored in the image processing section, the control section may hold all of these programs to control the entire spectral fundus image measuring apparatus including the image processing section, or the control section may read these programs from an external recording device or CD ROM to control the spectroscopic fundus measuring apparatus. The interval at which the spectral fundus images are taken is not limited to 10 nm, and the spectral fundus images may be taken at intervals of, for example, 2.5 nm or 25 nm.

This invention is used in measuring spectral fundus images.

DESCRIPTION OF REFERENCE NUMERALS AND SYMBOLS

1: spectral fundus image measuring apparatus (spectroscopic fundus image measuring apparatus)
2: fundus camera section
3: top housing section
4: photographing section
5: relay optical section
6: camera relay section
7: image processing section
7A: storage section
7B: display section
8: control section
9: extended section
10: illumination optical system
11: illumination light source (halogen lamp)
12: condenser lens
13: spectral characteristic correcting filter
14: diaphragm
15: mirror
16: relay lens
20: light receiving optical system
21: iris diaphragm
22: focusing lens
23: image forming lens
24: mirror
25: switching mirror
31: dichroic mirror
32: liquid crystal wavelength tunable filter
33: image forming lens
34: CCD camera
40: common optical system
41: beam splitter
42: objective lens
50: alignment optical system
51: alignment light source
52: dichroic mirror
53: image forming lens
54: monitoring camera
60: finder optical system
71: photographed image taking section
72: position correcting section
73: image analyzing section
74A: first grouping section
75A: second grouping section
76A: specific part image forming section
77: processing section
78: image synthesizing section
81: exposure control section
82: wavelength control section
E: subject eye
F: fundus

What is claimed is:

1. A spectroscopic fundus measuring apparatus, comprising:
an illumination optical system having an illumination light source for illuminating a fundus;
a light receiving optical system for receiving a wavelength-tunable light beam reflected from the illuminated fundus to photograph a series of spectral fundus images of different wavelengths;
an image processing section for processing the spectral fundus images; and
a storage section for storing the spectral fundus images,
wherein the image processing section has a position correcting section for correcting the series of spectral fundus images photographed by the light receiving optical system to match the positions of the same parts therein, and an image analyzing section for calculating the spectral characteristic of each part in the spectral fundus images based on the series of spectral fundus images corrected in the position correcting section,
wherein the storage section stores the spectral characteristics of the parts together with standard spectral characteristics of specific parts, and
wherein the image processing section has a first grouping section for comparing the spectral characteristic of each part with the standard spectral characteristics of the specific parts to divide the parts into groups corresponding to the specific parts,
wherein the first grouping section divides the parts into groups of retinal artery, retinal vein, macula area, optic nerve head and so on as the specific parts.

2. The spectroscopic fundus measuring apparatus as recited in claim 1,
wherein the image processing section has a specific part image forming section for collecting respectively the parts divided into groups corresponding to the specific parts to form images of the specific parts.

3. The spectroscopic fundus measuring apparatus as recited in claim 1, further comprising:
a display section for displaying the spectral fundus images, wherein the image analyzing section calculates the contrast between the brightness of each of the parts and the brightness of the background thereof based on the series of spectral fundus images corrected in the position correcting section, wherein the storage section stores the contrasts of the parts, and wherein, when an operator designates a part on the displayed spectral fundus images, the display section displays the contrast of the designated part stored in the storage section.

4. The spectroscopic fundus measuring apparatus as recited in claim 2, wherein the image processing section has an image synthesizing section for synthesizing the images of the specific parts to form a synthesized fundus image.

5. The spectroscopic fundus measuring apparatus as recited in claim 1, wherein the wavelength of the illumination light beam from the illumination light source is tunable or the illumination optical system or the light receiving optical system has a wavelength selective filter.

6. A spectroscopic fundus measuring apparatus, comprising:

an illumination optical system having an illumination light source for illuminating a fundus;

a light receiving optical system for receiving a wavelength-tunable light beam reflected from the illuminated fundus to photograph a series of spectral fundus images of different wavelengths;

an image processing section for processing the spectral fundus images; and a storage section for storing the spectral fundus images, wherein the image processing section has a position correcting section for correcting the series of spectral fundus images photographed by the light receiving optical system to match the positions of the same parts therein, and a second grouping section for regarding each principal component image formed by a principal component analysis method as a fundus image of a specific part based on the series of spectral fundus images corrected in the position correcting section to divide parts in the spectral fundus images into groups corresponding to the specific parts, wherein the second grouping section regards a choroidal vessel image, a retinal artery image, a retinal vein image and a retinal blood vessel image respectively as corresponding to any one of a second principal component image to a fifth principal component image to divide the parts into groups.

7. The spectroscopic fundus measuring apparatus as recited in claim 6, further comprising:

a display section for displaying the spectral fundus images, wherein the image processing section has an image analyzing section for calculating a spectral characteristic of each part in the spectral fundus images based on the series of spectral fundus images corrected in the position correcting section, wherein the storage section stores the spectral characteristics of the parts together with standard spectral characteristics of specific parts, and wherein, when an operator designates a part on the displayed spectral fundus images, the display section displays the spectral characteristic of the designated part stored in the storage section.

8. The spectroscopic fundus measuring apparatus as recited in claim 7, wherein the image analyzing section calculates the contrast between the brightness of each of the parts and the brightness of the background thereof based on the series of spectral fundus images corrected in the position correcting section, wherein the storage section stores the contrasts of the parts, and wherein, when an operator designates a part on the displayed spectral fundus images, the display section displays the contrast of the designated part stored in the storage section.

9. The spectroscopic fundus measuring apparatus as recited in claim 6, wherein the image processing section has an image synthesizing section for synthesizing the images of the specific parts to form a synthesized fundus image.

10. The spectroscopic fundus measuring apparatus as recited in claim 6, wherein the wavelength of the illumination light beam from the illumination light source is tunable or the illumination optical system or the light receiving optical system has a wavelength selective filter.

11. A spectroscopic fundus measuring method, comprising:

a step of illuminating a fundus of a subject eye of an animal with a light beam from an illumination light source emitting a light beam in a specified wavelength range;

a step of photographing a series of spectral images of the fundus of the animal of different wavelengths by receiving a wavelength-tunable light beam reflected from the illuminated fundus;

an image processing step of processing the spectral fundus images; and a storing step of storing the spectral fundus images, wherein the image processing step has a position correcting step of correcting the series of spectral fundus images photographed in the photographing step to match the positions of the same parts therein, and an image analyzing step of calculating the spectral characteristic of each part in the spectral fundus images based on the series of spectral fundus images corrected in the position correcting step;

wherein the spectral characteristics of the parts are stored together with standard spectral characteristics of specific parts in the storing step, and wherein the image processing step has a first grouping step of comparing the spectral characteristic of each part with the standard spectral characteristics of the specific parts to divide the parts into groups corresponding to the specific parts, wherein the image processing step has a specific part image forming step of collecting respectively the parts divided into groups in the first grouping step or the second grouping step to form images of the specific parts, and an image synthesizing step of synthesizing the images of the specific parts to form a synthesized fundus image.

12. A spectroscopic fundus measuring method, comprising:

a step of illuminating a fundus of a subject eye of an animal with a light beam from an illumination light source emitting a light beam in a specified wavelength range;

a step of photographing a series of spectral images of the fundus of the animal of different wavelengths by receiving a wavelength-tunable light beam reflected from the illuminated fundus;

an image processing step of processing the spectral fundus images; and a storing step of storing the spectral fundus images, wherein the image processing step has a position correcting step of correcting the series of spectral fundus images photographed in the photographing step to match the positions of the same parts therein, and a second grouping step of regarding each principal component image formed by a principal component analysis method as a fundus image of a specific part (that is, regarding data corresponding to specific parts having a common spectral characteristic as being reflected in the n-th order principal component data) based on the series of spectral fundus images corrected in the position correction step to divide parts in the spectral fundus images into groups corresponding to the specific parts, wherein the image processing step has a specific part image forming step of collecting respectively the parts divided into groups in the first grouping step or the second grouping step to form images of the specific parts, and an image synthesizing step of synthesizing the images of the specific parts to form a synthesized fundus image.

* * * * *